United States Patent [19]

Alpert

[11] Patent Number: 5,692,502

[45] Date of Patent: Dec. 2, 1997

[54] COMPUTER-AIDED DRUG RECOGNITION SCREEENING EVALUATION SYSTEM AND METHOD

[76] Inventor: Scott E. Alpert, 9508 Clocktower La., Columbia, Md. 21046

[21] Appl. No.: 526,317

[22] Filed: Sep. 11, 1995

[51] Int. Cl.$^6$ .................................................. G06F 15/42
[52] U.S. Cl. ..................................... 128/630; 364/413.02
[58] Field of Search ......................... 128/630; 364/413.02

[56] References Cited

U.S. PATENT DOCUMENTS

| | | | |
|---|---|---|---|
| 4,290,114 | 9/1981 | Sinay | 364/413.02 |
| 4,715,386 | 12/1987 | Martin . | |
| 4,733,354 | 3/1988 | Potter et al. . | |
| 4,988,628 | 1/1991 | Nanji . | |
| 5,005,143 | 4/1991 | Altschuler et al. . | |
| 5,023,785 | 6/1991 | Adrion et al. . | |
| 5,057,437 | 10/1991 | Binder . | |
| 5,137,345 | 8/1992 | Waldorf et al. . | |
| 5,187,506 | 2/1993 | Carter . | |
| 5,255,187 | 10/1993 | Sorensen | 364/413.02 |
| 5,265,010 | 11/1993 | Evans-Paganelli et al. | 364/413.02 |
| 5,299,121 | 3/1994 | Brill et al. . | |

FOREIGN PATENT DOCUMENTS

| | | |
|---|---|---|
| 0 233 063 | 8/1987 | European Pat. Off. . |
| 1426177 | 2/1976 | United Kingdom . |

Primary Examiner—Angela D. Sykes
Assistant Examiner—Eric F. Winakur
Attorney, Agent, or Firm—Richard C. Litman

[57] ABSTRACT

A non-invasive screening system and method for suspected drug users includes computer software, which when executed displays a series of categories each listing one or more physical elements capable of being observed by a trained operator. Partial categories include ATTITUDE, SPEECH and ODOR and exemplary elements thereunder comprise (1)sedated, euphoric, irritable; (2)deliberate, sluggish, repetitive; (3)alcohol, chemical, glue, respectively. As the various categories and their physical elements are displayed among various menus presented on a computer monitor, the operator tags only those elements which are observed to exist in the suspect. When all menus have been responded to by the operator, the software notes which elements of each category have been tagged and with this data at hand, applied weights to the responses in accordance with a database history of which elements are most contributory to a positive conclusion with respect to each of a plurality of drug classes. A graphical output is delivered by the computer, depicting the probability of recent use of drugs in each of a plurality of drug classes, with the graph illustrating each drug class probability in either a negative, marginal or positive sub-range on the graph. Operator input which may lead to an inconclusive determination results in a message that urine screening or medical evaluation is called for while following the graphical display of a positive determination, a narrative is presented explaining the rationale of the test, the drugs potentially responsible for the results and recommendations as to further action.

8 Claims, 25 Drawing Sheets

CANNABINOIDS SCORING

CENTRAL NERVOUS SYSTEM STIMULANT (CNSS) SCORING

INHALANT SCORING

PHENCYLIDINE (PCP) SCORING

HIPPUS

HIPPUS [ ]   REBOUND HIPPUS [ ]

NASAL OBSERVATIONS

NORMAL [ ]   POWDERY [ ]   RED [ ]   SWOLLEN [ ]   HAIRLESS [ ]   SCARRED [ ]

ORAL OBSERVATIONS

RED [ ]   RESIDUE [ ]   BURN [ ]   UVULA OUTLINE [ ]

ODOR OBSERVATIONS

ALCOHOL [ ]   CHEMICAL [ ]   MARIJUANA [ ]   GAS OR GLUE [ ]

EYE OBSERVATIONS

BLOODSHOT [ ]   GLASSY [ ]   BLANK [ ]   WATERY [ ]   DROOPY [ ]   INFLAMED [ ]

HORIZANTAL GAZE NYSTAGMUS

NONE [ ]   SLLIGHT [ ]   MODERATE [ ]   HEAVY [ ]

| SPEECH |
| --- |
| DELIBERATE |
| SLUGGISH |
| CLEAR / STEADY |
| SLOW |
| THICK / SLURRED |
| REPETITIVE |
| RASPY |
| RAPID |
| UNRESPONSIVE |
| INCOHERENT |

*Fig. 3*

| PULSE |
| --- |
| RATE (BPM) |

*Fig. 4*

| INJECTIONS |
| --- |
| BLOOD |
| SERUM |
| SHINY CRUST |
| SCAB |
| ELEVATED |
| DRIED |

*Fig. 5*

| PUPIL SIZE (BOTH L & R) |
| --- |
| ROOM LIGHT |
| DARKNESS |
| DIRECT |

*Fig. 6*

| REACTION TO LIGHT |
| --- |
| NONE |
| SLIGHT |
| SLUGGISH |
| NORM. REACTIVE |

*Fig. 7*

| NASAL CAVITY POWDERY RESIDUE |
| --- |
| RED |
| SWOLLEN |
| HAIRLESS |
| SCARRED |
| NORMAL |

*Fig. 8*

| ATTITUDE |
| --- |
| NOT UNUSUAL |
| SEDATED |
| AGITATED |
| HALLUCINATING |
| EUPHORIC |
| COMBATIVE |
| IRRITABLE |
| ARGUMENTATIVE |
| STUPOROUS |
| ERRATIC |
| DISORIENTED |
| BIZZARRE |
| PASSIVE |
| DEPRESSED |
| EXCITED |

*Fig. 15*

| OTHER SYM. |
| --- |
| SCRATCHING |
| DRY MOUTH |
| RUNNY NOSE |
| SNIFFING |
| NODDING |
| PERSPIRING |
| LIP SMACKING |
| POOR COORD. |
| SLOW RESPONSES |
| PILOERECTION |

*Fig. 16*

| HIPPUS |
| --- |
| HIPPUS |
| REBOUND HIPPUS |

*Fig. 17*

| THIRTY SECOND TIME COUNT |
| --- |
| NORMAL |
| DISTORTED |
| FAST |
| SLOW |

*Fig. 18*

COMPUTER-AIDED DRUG RECOGNITION SCREEENING EVALUATION SYSTEM AND METHOD

BACKGROUND OF THE INVENTION

1. Field of the Invention

This invention relates generally to an improved system whereby illicit drug use may be clinically diagnosed by a trained operator through non-invasive or passive observations carried out in a sequence as advanced by a computer program and wherein specific ones of prescribed responses to these observations are weighted by software, which analyzes all of the input to present a diagnosis indicative of recent drug use, when applicable. The instant development serves to integrate technology recognized by the Los Angeles Police Department as being useful in the detection of drivers who were under the influence of illicit drugs and as herein refined by forensic clinicians, provides a drug recognition procedure that is acceptable by numerous authorities including, both federal and state courts, the National Highway Traffic Safety Administration and the Association of Chief's of Police.

2. Description of the Prior Art

It is acknowledged that any of various physical symptoms have long been identified as indicative of at least suspected recent use of one or more of several illicit drugs. Such symptoms include but are not limited to, irregular pulse or rate of breathing, nostril discharge and dilated or constricted pupils. Without conducting invasive examination procedures such as the testing of blood and urine specimens, even a trained observer relying upon numerous physical conditions, has had to base any opinion as to probably illicit drug use on their experience of having encountered hundreds of previous suspects. Such a hit or miss type of procedure falls far short of providing the accuracy of diagnosis as offered by the present integrated system, wherein an accurate evaluation and results may be accomplished by a trained operator within ten minutes.

A drug detection method is taught in UK Patent No. 1,426,177 published on Feb. 25, 1976 and which discloses the identification of specific categories of drug samples by carrying out a field test utilizing the application of a reagent to a drug specimen as applied to filter paper. This is in contrast to the present system which is not concerned with identifying a drug sample but rather, the possible use of any of a plurality of illicit drugs by a suspect and wherein no specimens of any type are utilized.

European Patent Application Nr. 87301024.3 published Aug. 19, 1987 under Publication Nr. 0,233,063 advances a further example of a drug identification system wherein a suspect drug specimen is tested by means of a reagent to visually signify when the specimen is of a particular class of drugs. Again, this procedure is unlike that as proposed herein, as described immediately heretofore.

An example of the use of a computer to aid in the detection of drug abuse will be found in U.S. Patent No. 4,715,386 issued Dec. 29, 1987 to Martin and wherein electronystamograph waveforms as measured from a suspected drug user are converted to digitally recorded waveforms for comparison with waveform data as stored on a computer. The resulting comparison yields an indication of suggested drug ingestion. The Martin system is strikingly unlike that as now proposed in that waveforms and the careful measurement thereof form no part of the present development.

A further example of the use of a programmed computer to arrive at a medical diagnosis is shown in U.S. Pat. No. 4,733,354 issued to Potter et al. on Mar. 22, 1988 and involves a dermatopathological diagnosis whereby an operator observes a biopsy specimen and triggers menu options resulting in a presented diagnosis. This system is unlike that proposed herein as Potter et al. employs a single, invasively secured specimen, contrary to the instant procedure which is totally passive and relies upon the observation of a plurality of characteristics of each of several physical conditions.

U.S. Pat. No. 4,988,628 issued Jan. 29, 1991 to Nanji teaches a drug detection method that employs a fluid specimen which is initially separated such as by chromatography or differential centrifugation and thereafter subjected to ion mobility spectrometry. This is significantly unlike the present proposal wherein no body fluid sample is called for nor is any sophisticated laboratory equipment required. Additionally, the Nanji method lacks the interactive computer software involved herein.

An interactive, computer based system for use by medical personnel is shown in U.S. Pat. No. 5,005,143 issued to Altschler et al. on Apr. 2, 1991, wherein a database containing the opinions of many experts covering numerous medical conditions is drawn upon through a menu selection procedure, in order to allow a using medical professional to arrive at their own evaluation or course of action in any one specific situation. Although certainly non-invasive, this method differs from the current procedure wherein the involved software is not a database of case histories or specific instances of particular ailments but rather presents a structured sequence of menus containing outward physical attributes, the selection of which applies weights to the answers and leads to a graphical representation depicting the likelihood of exposure to illicit drug use within the past 72 hours.

In the case of U.S. Pat. No. 5,023,875 issued to Adrion et al. on Jun. 11, 1991, hematology diagnosis is carried out with the assistance of computer software. Initially, a serum specimen is subjected to apparatus, such as a centrifuge, to secure quantitative data for a plurality of blood parameters and with this data at hand, the software is used to analyze the parameters in light of a database of expert opinions comparing the parameter values. This is contrary to the present development wherein no invasive specimens are involved but instead, visual, passive observations are manipulated by computer software to arrive at a graphical presentation indicative of probable use of illicit drugs.

An analytical method specifically for the detection of drugs will be found in U.S. Pat. No. 5,057,437 issued Oct. 15, 1991 to Binder and wherein liquid chromatography is employed to analyze a wide range of drugs. The method involves a plurality of strictly laboratory procedures and thus wholly departs from the current invention as addressed hereinabove.

Another example of means for detecting drug impairment is advanced in U.S. Pat. No. 5,137,456 issued to Waldorf et al. on Aug. 11, 1992 and which utilizes a specific apparatus employing infrared radiation along with a camera to record parameters associated with the suspect's pupil/iris. This disclosure is unlike the instant development wherein numerous physiological parameters are visually observed and manipulated by computer software to arrive at a diagnosis relative a plurality of different categories of drugs.

A further example of detecting drug or alcohol impairment through an apparatus measuring pupil reaction to radiated light will be found in U.S. Pat. No. 5,187,506 issued Feb. 16, 1993 to Carter. The apparatus used by this reference also employs a computer and presents graphical output reflecting the pupil diameter. This is in contrast to the current system which involves the visual, manual identification of numerous physical parameters with computer software applying weights to the operator's input throughout several menus to present a graphical output reflecting the probability of use of any of several classes of drugs.

A general computer-aided system applicable to the medical field is shown in U.S. Pat. No. 5,299,121 issued to Brill et al. on Mar. 29, 1994 and wherein a customer inputs characteristics relating to an ailment following which the computer executes a symptom knowledgebase which may call for added input, prior to over-the-counter products being recommended to the user for treatment of their ailment. Not only does this reference fail to address the drug detection aspect of the present invention, the software avoids the multi-choice menus combined with multiple levels of input leading to graphical representation of one or more drugs having been recently consumed.

None of the above inventions and patents, taken either singly or in any combination, is seen to even remotely suggest or describe the instant invention as claimed herein.

SUMMARY OF THE INVENTION

A drug recognition screening evaluation system is proposed whereby it can be determined whether an individual is under the influence of drugs or has recently used drugs. An operator or interrogator using the procedure will be able to accurately determine the specific class of drug that has been ingested following a series of visual observations, without any invasive testing of the suspect individual. The associated software presents a plurality of menus offering choices covering a plurality of physical parameters in each of several categories, with the software applying weights to specific responses, prior to calculating the final output which comprises a graphical representation depicting the likelihood of one or more drugs having been ingested by the individual. The final output is appropriately influenced by certain medical conditions that may interfere with the validity of the evaluation and so responds with suitable advice for further action. The system does not require the services of a physician but does call for operation by a trained drug recognition expert, particularly for its most efficient use, since careful physical observations are a must to insure the most accurate results.

The parameters observed by the trained operator and which are symptomatic indicators of recent drug use comprise appearance, behavior, performance or psychophysical tests, eye movement, pupil size, pupil reaction to light, vital signs and damage to the skin or mucous membranes. The resultant graphical display produced by the software separately lists the seven different drug classes, plus an opiate withdrawal class with a y-axis depicting a percentage range for each class. With the graph divided into three y-axis ranges, those classes falling into the lowest range will thus represent no drug use while those falling into the middle range would indicate a marginal conclusion to drug use and finally, those classes falling into the upper range would indicate a positive drug use with a recommendation for referral to urine testing.

The software analyzes the responses to a total of 89 symptoms advanced on a CRT and presented among a plurality of physical categories, before displaying the final graphical analysis. The final calculations are carried out with only selected ones of the plurality of symptom elements being applicable in determinations relative each drug class, while the tagged symptoms are assigned variable weights as the software determines a score for the probability of each drug class.

Accordingly, one of the objects of the present invention is to provide an improved computer-aided system for drug screening including recording non-invasive physical observations with a readout being presented indicating the probable use by the suspect at hand, of any of a plurality of drug classes.

Another object of the present invention is to provide an improved computer-aided system for drug screening calling for the input of one or more symptoms in each of a plurality of categories of physical parameters.

A further object of the present invention is to provide an improved computer-aided system for drug screening wherein the system operator is presented with a plurality of menus offering numerous physical categories each displaying one or more symptoms with the software assigning different weights to each response so that during the final calculations, variable scoring is accomplished to arrive at a displayed probability of use of any of numerous classes of drugs.

Still another object of the present invention is to provide an improved computer-aided system for drug screening calling for operator input in response to menu-presented choices of observed physical parameters, with the software responding to any input which concludes that an accurate evaluation cannot be determined without a urine screen or medical evaluation.

A further object of the present invention is to provide an improved computer-aided system for drug screening wherein an operator's input to menus presenting choices of observed physical parameters pertinent to a suspect drug user results in a graphical representation reflecting probable use of any of a plurality of classes of drugs with each class depicted in one of three distinct ranges respectively denoting no drug use, marginal conclusion to drug use and positive indication of drug use with a recommendation for referral to urine testing.

These and other objects of the present invention will become readily apparent upon further review of the following specification and appended claims.

BRIEF DESCRIPTION OF THE DRAWINGS

Similar reference characters designate corresponding parts throughout the several figures of the drawings.

FIG. 2 is a chart illustrating an exemplary one of several displays presented to a system operator and containing several menu choices of certain of the screening categories of the program;

FIGS. 3–18 are charts depicting the plurality of categories of physical parameters considered by the system operator, together with the various option(s) of elements selectively tagged during operation of the software.

DETAILED DESCRIPTION OF THE PREFERRED EMBODIMENT

Figure 1A:
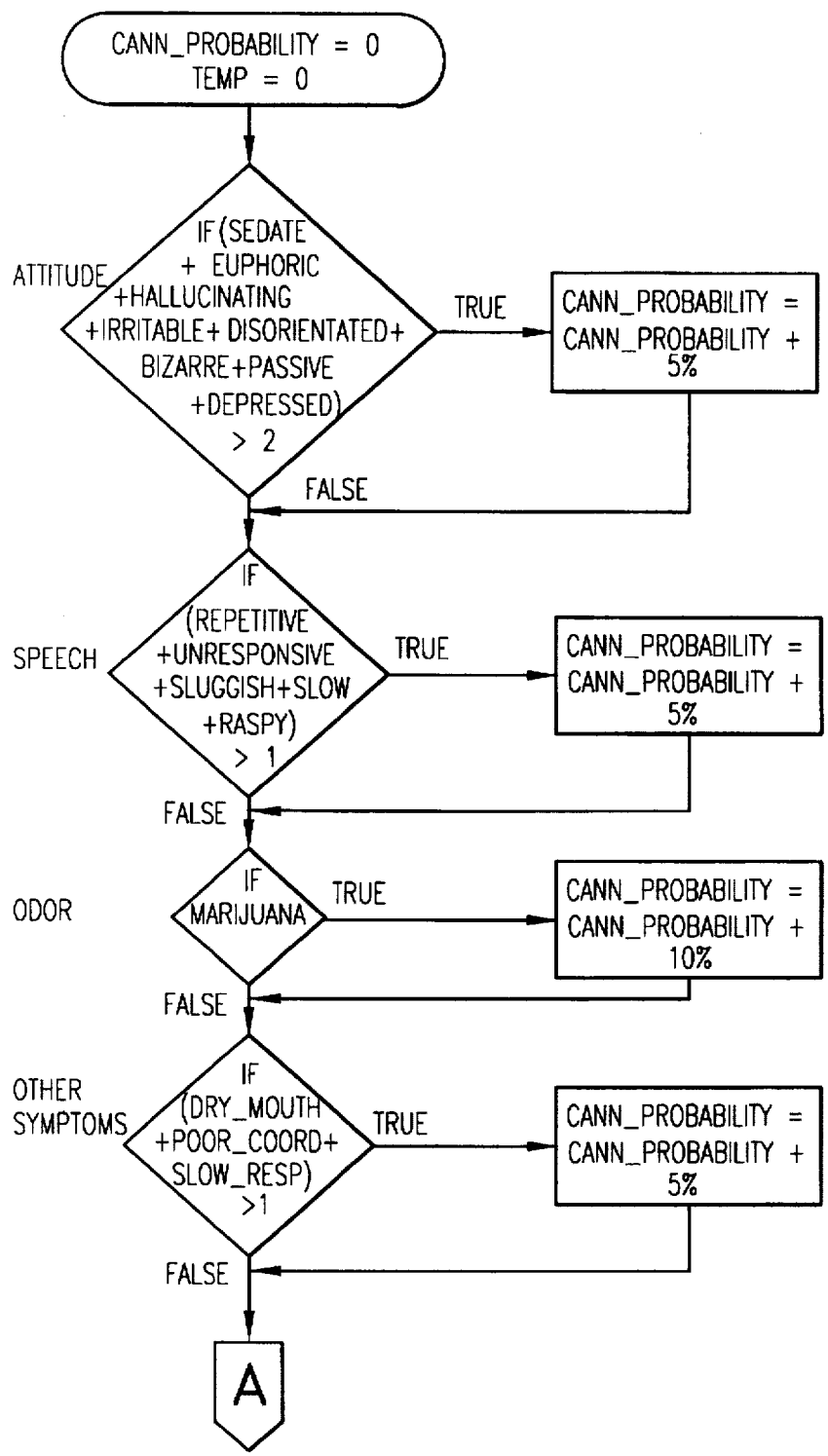
FIGS. 1-A through 1-T inclusive constitute is a flow chart of the computer program in an embodiment of the present invention.
Figure 1B:
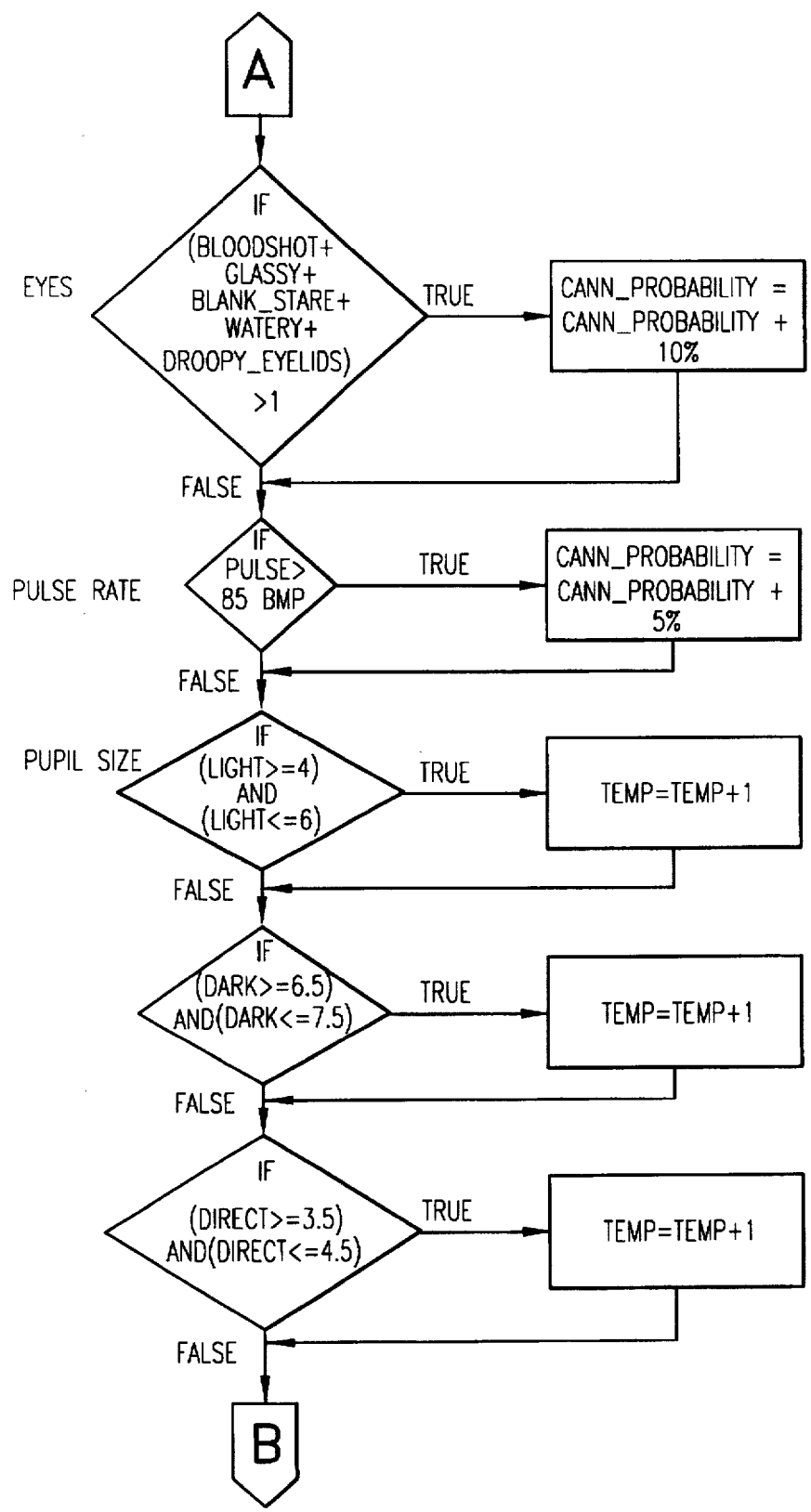
Figure 1C:
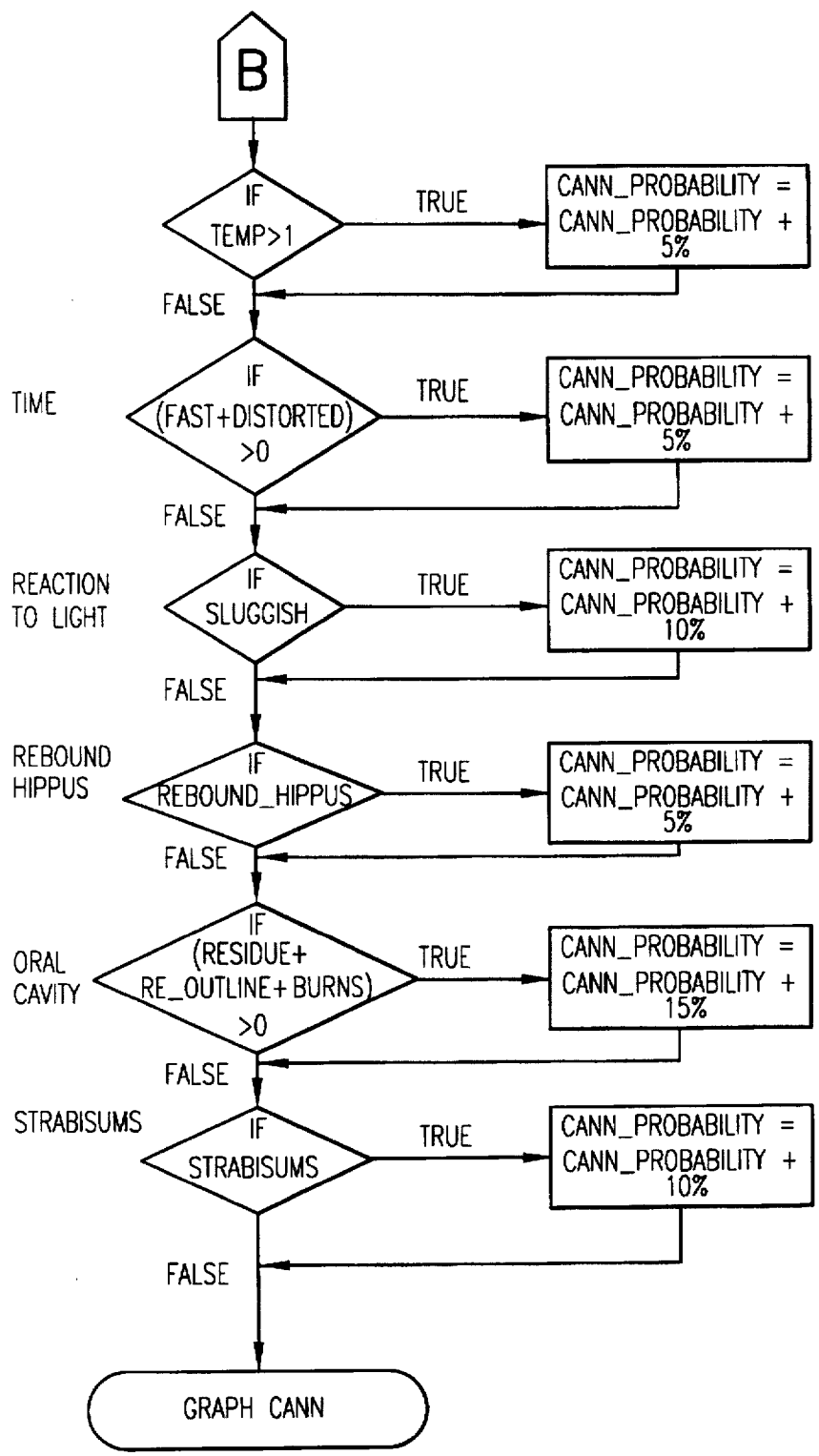
Figure 1D:
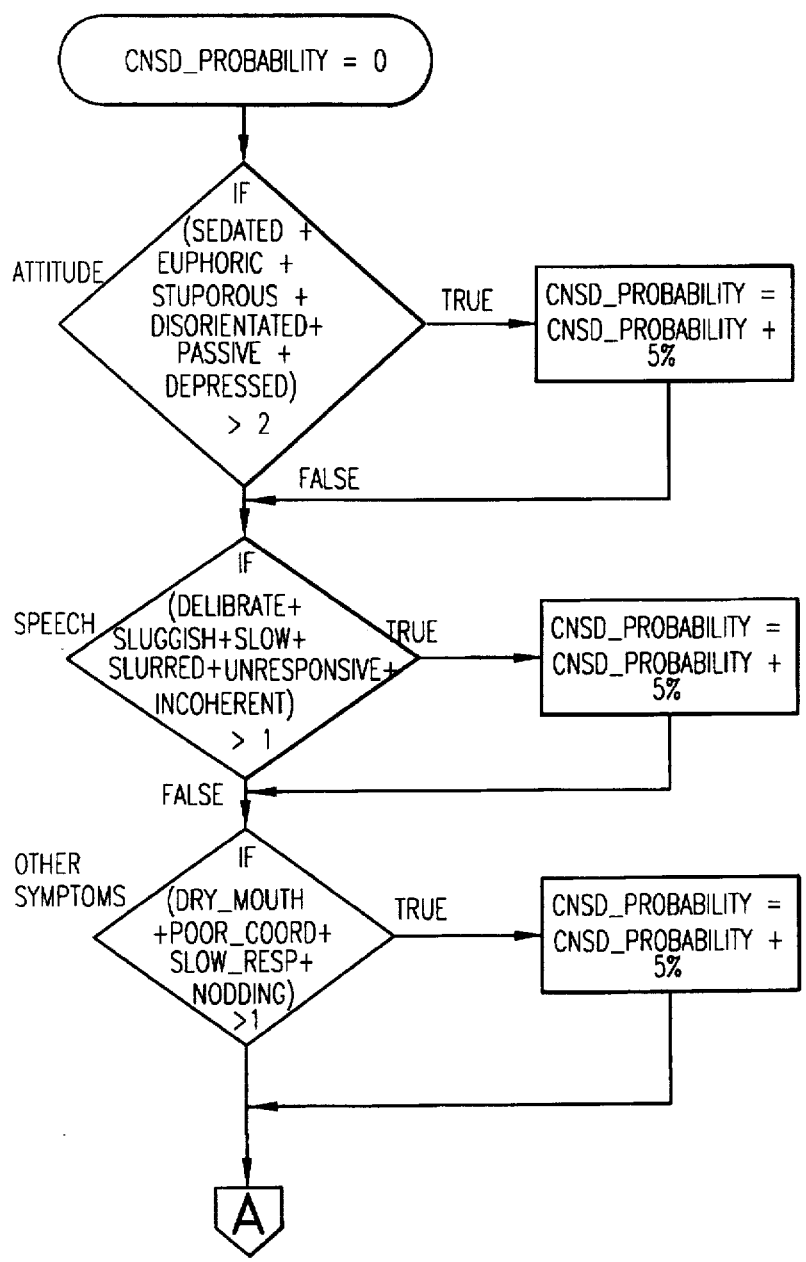
Figure 1E:
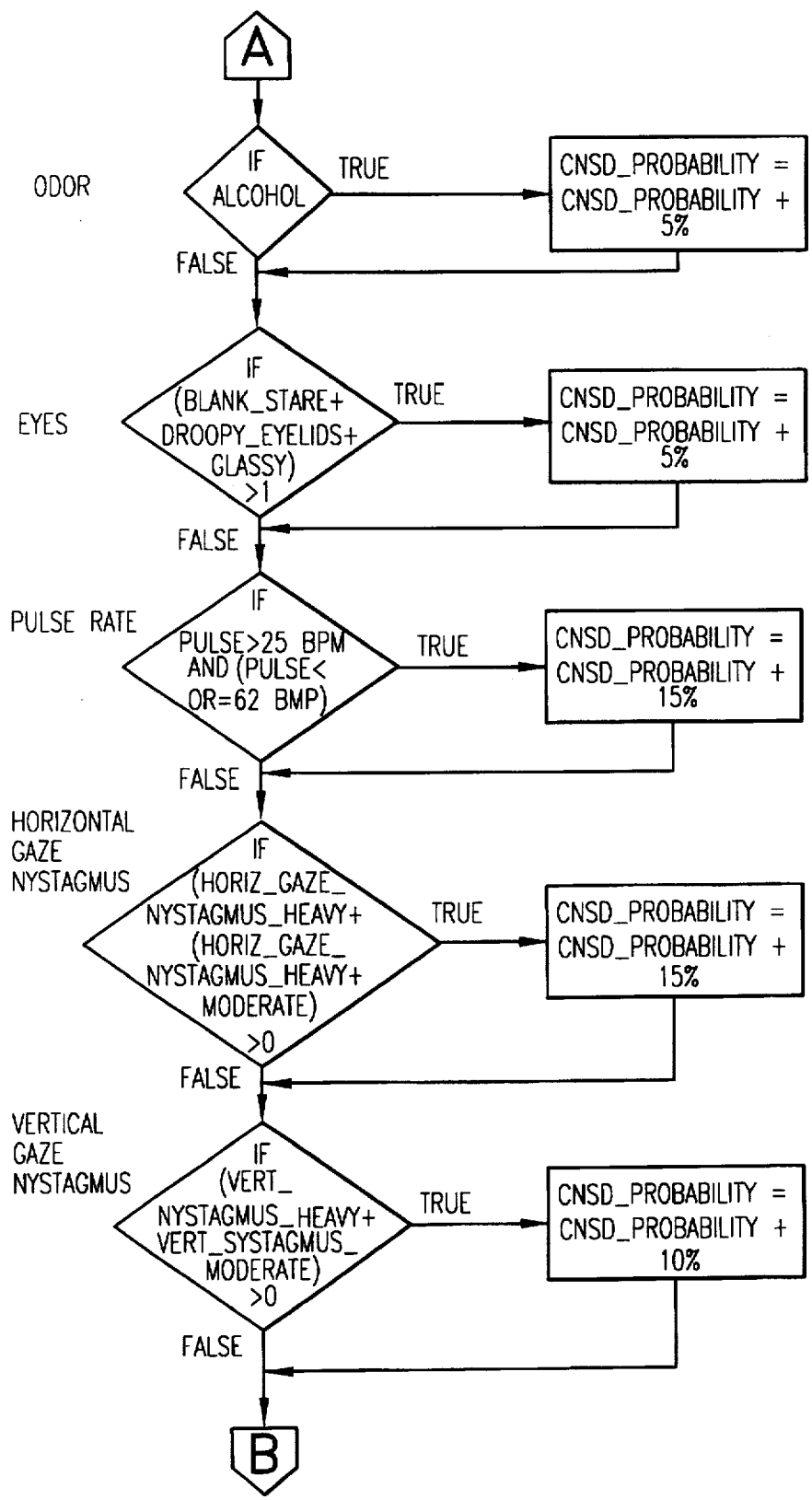
Figure 1F:
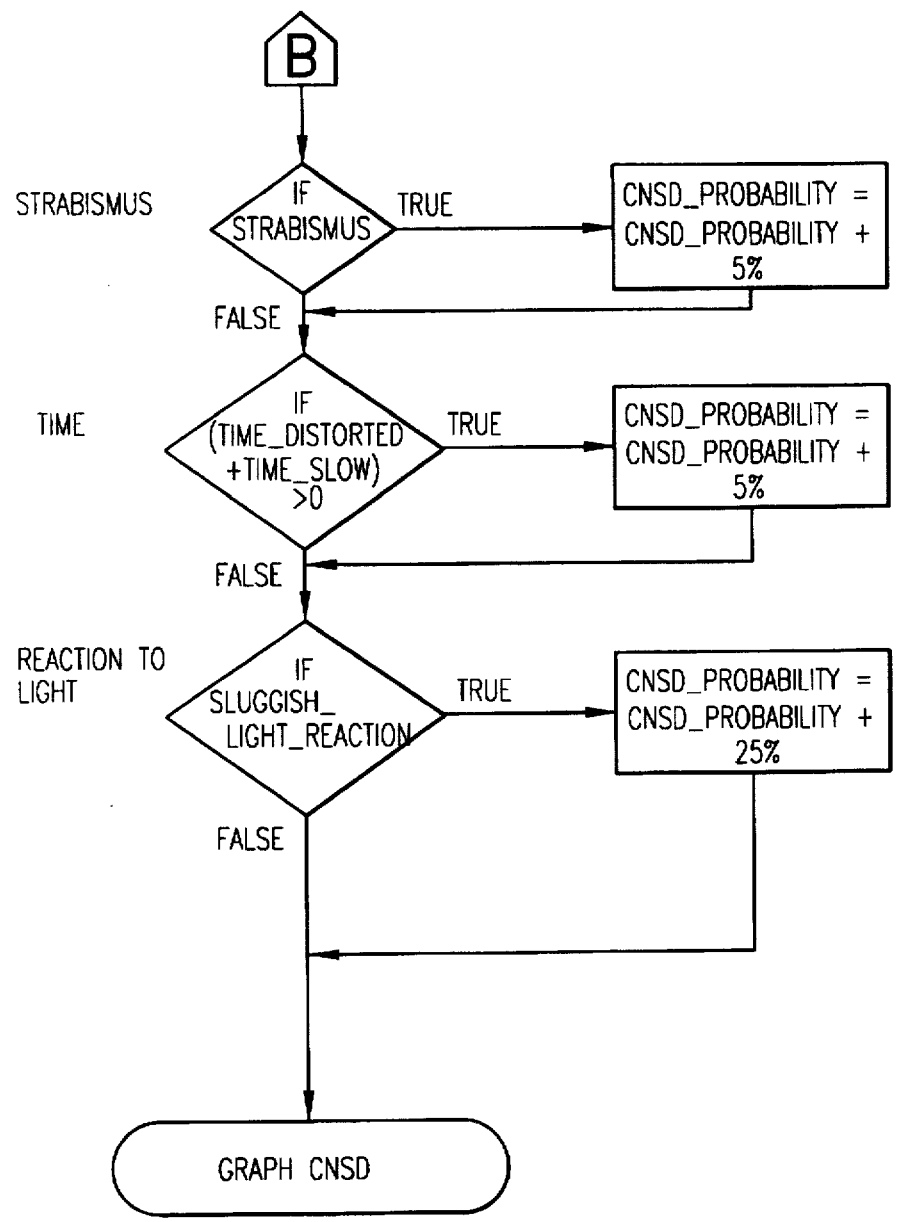
Figure 1G:
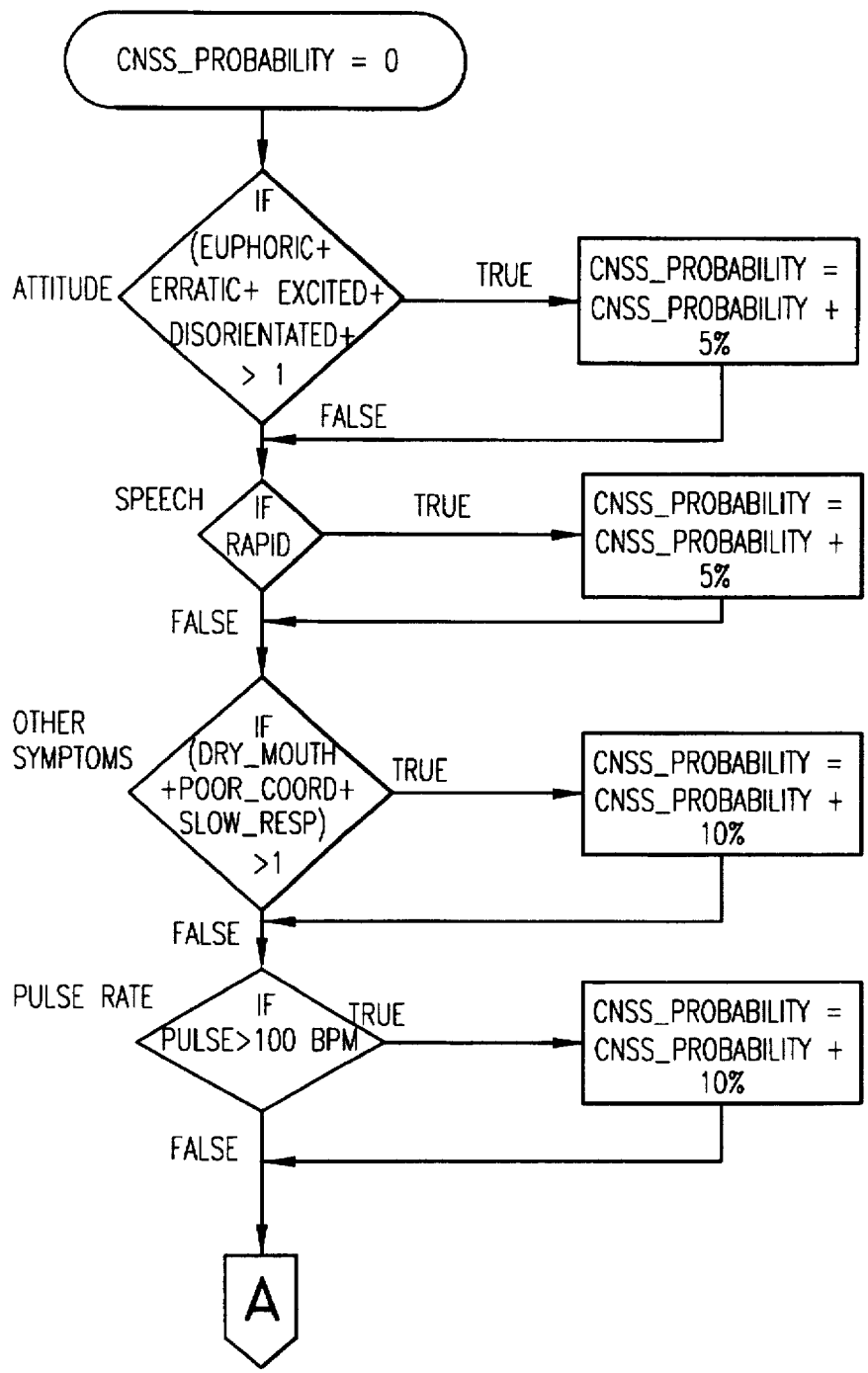
Figure 1H:
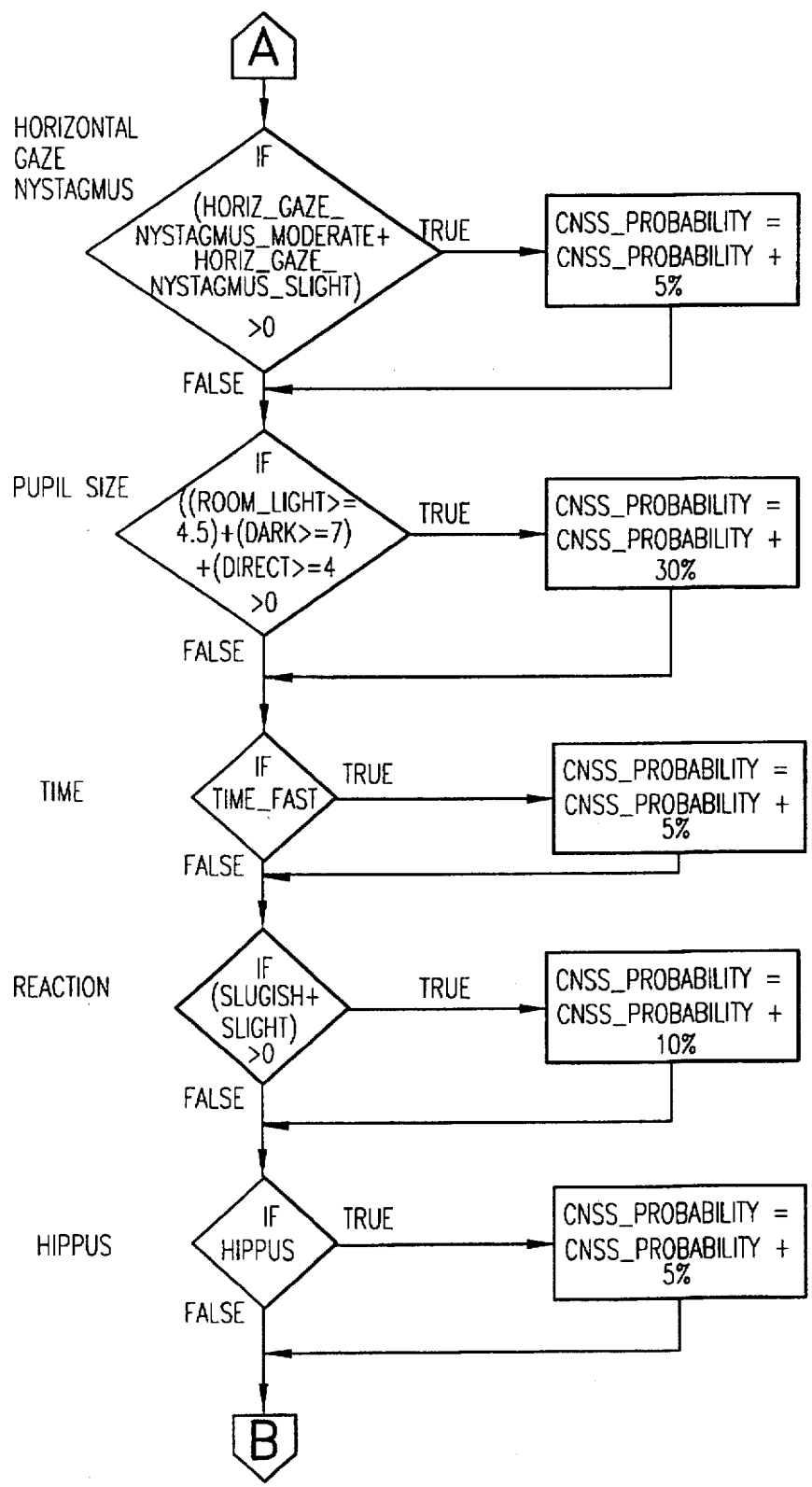
Figure 1I:
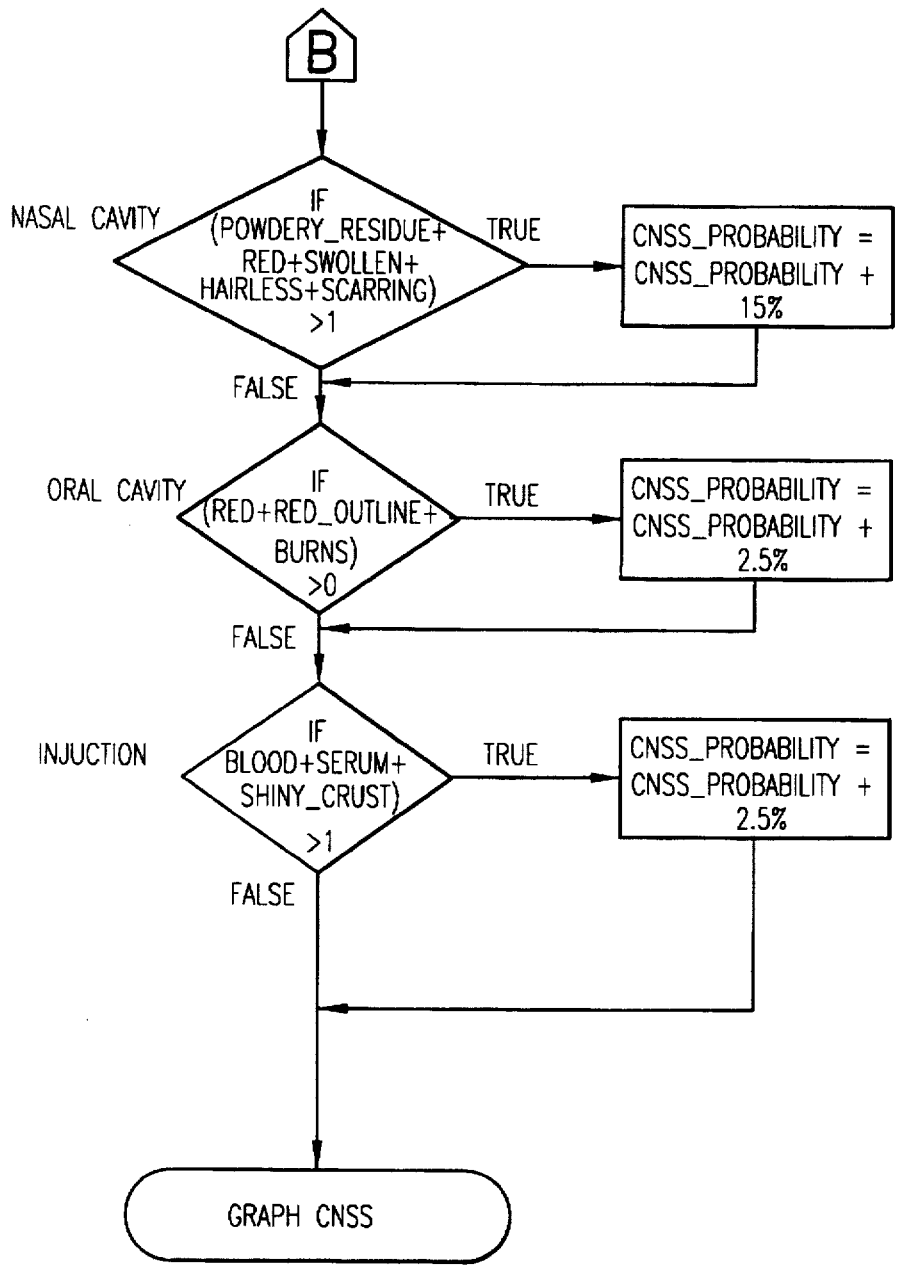
Figure 1J:
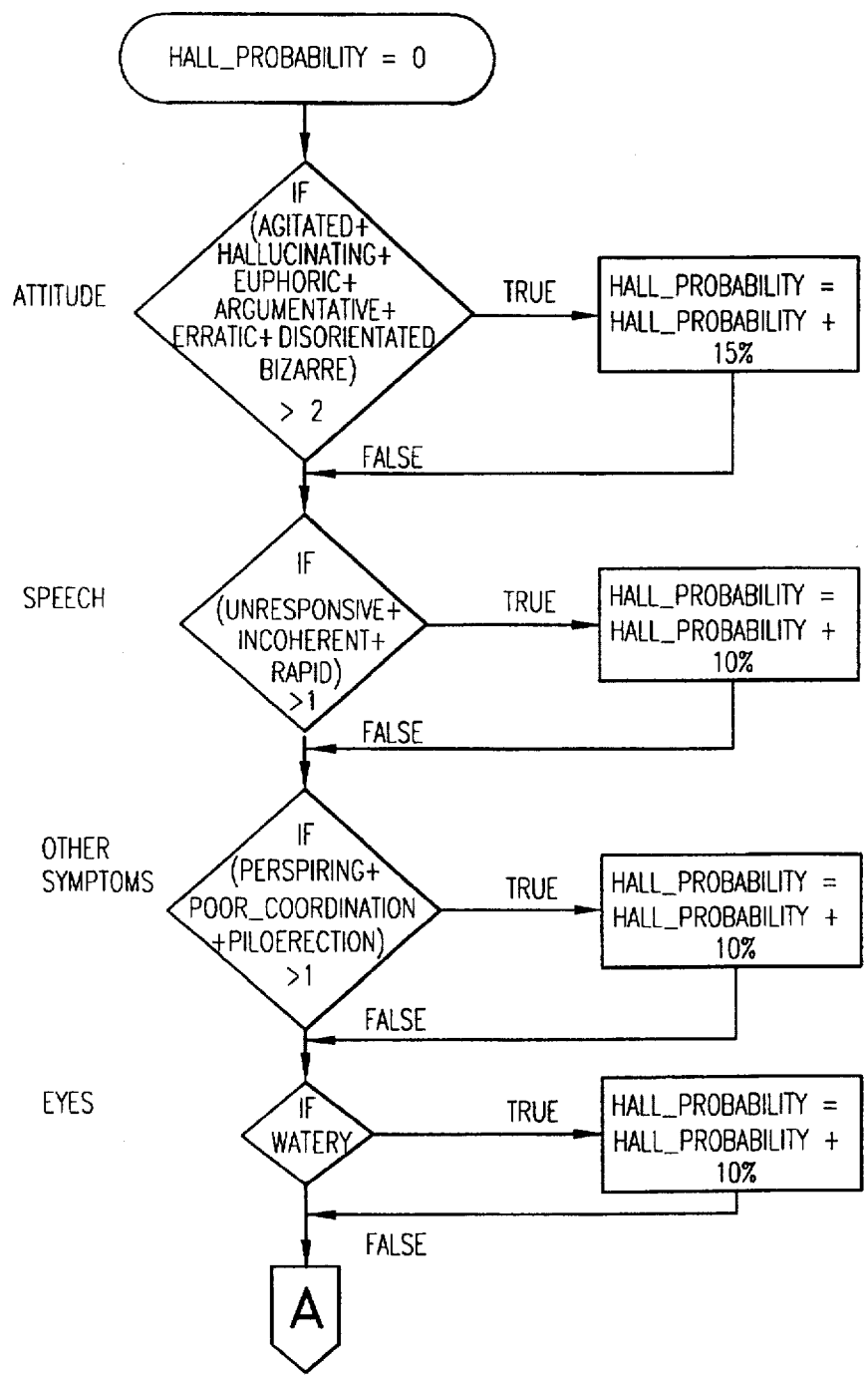
Figure 1K:
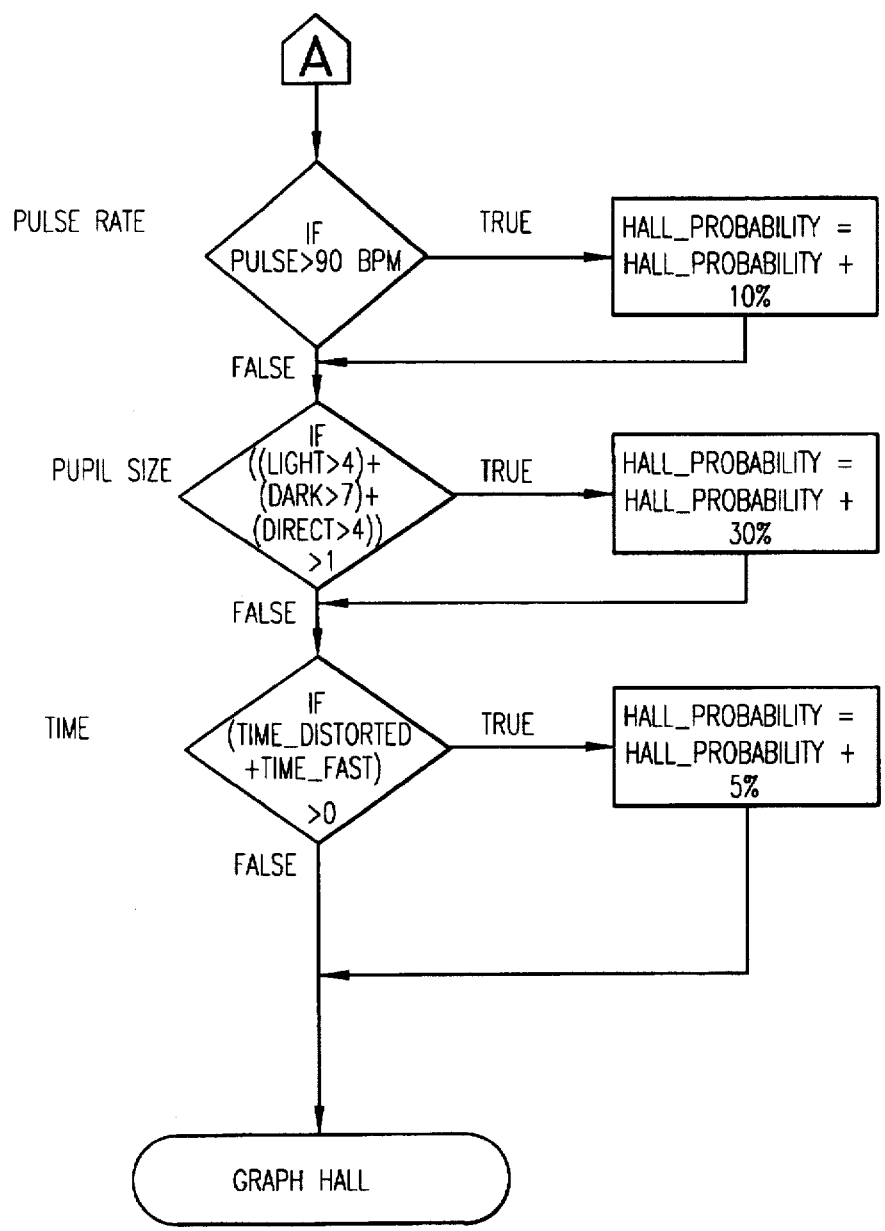
Figure 1L:
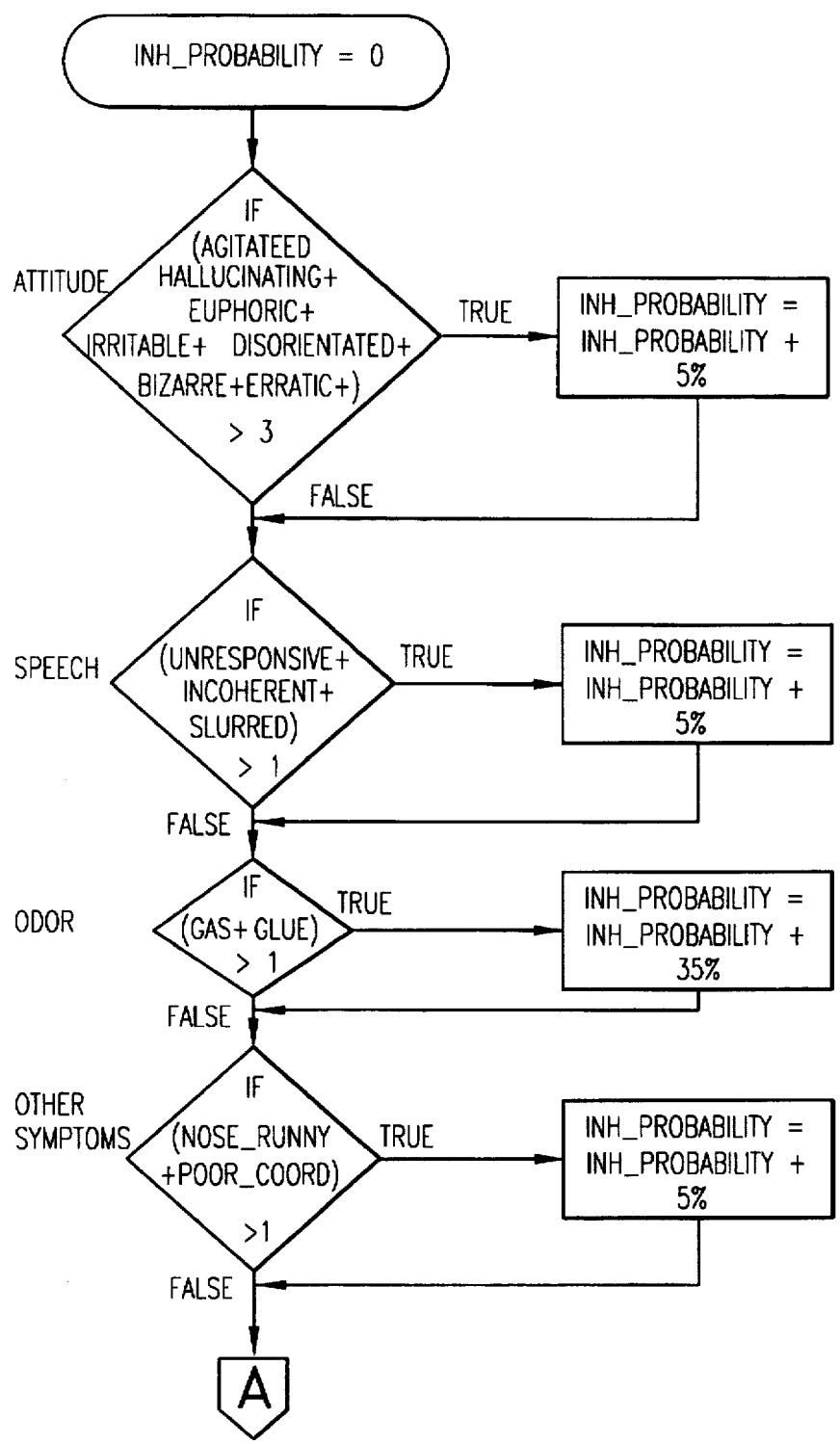
Figure 1M:
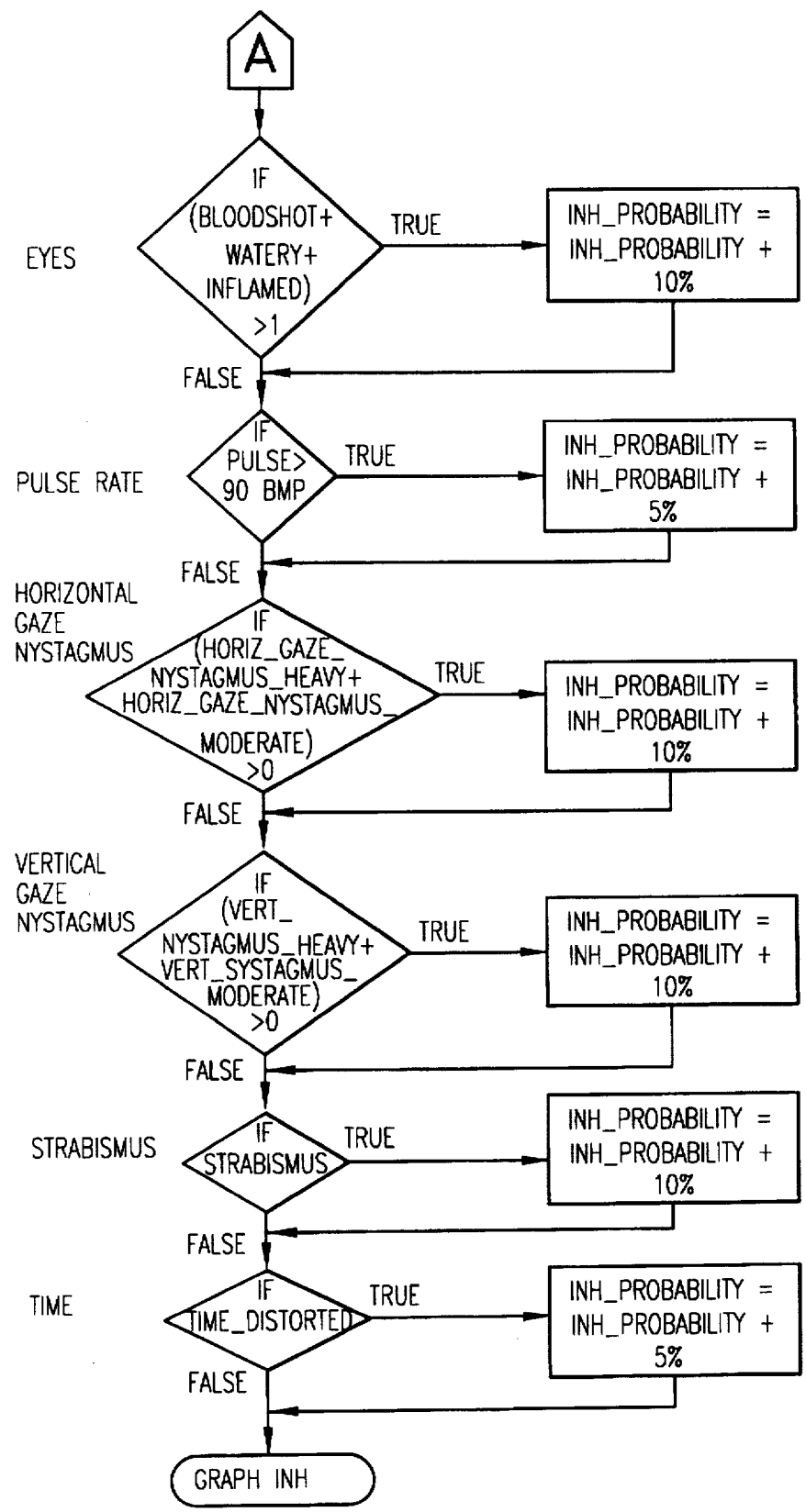
Figure 1N:
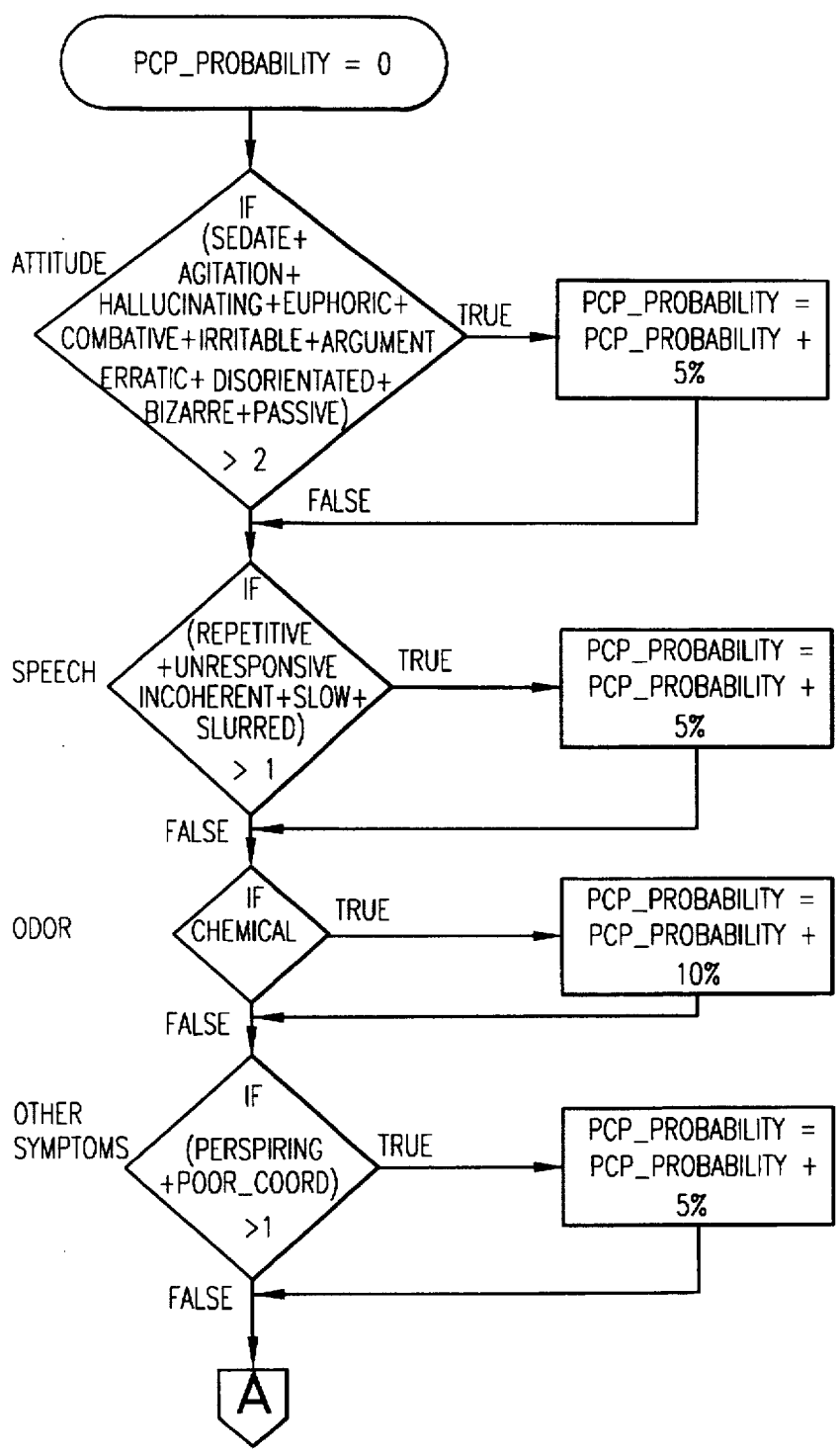
Figure 10:
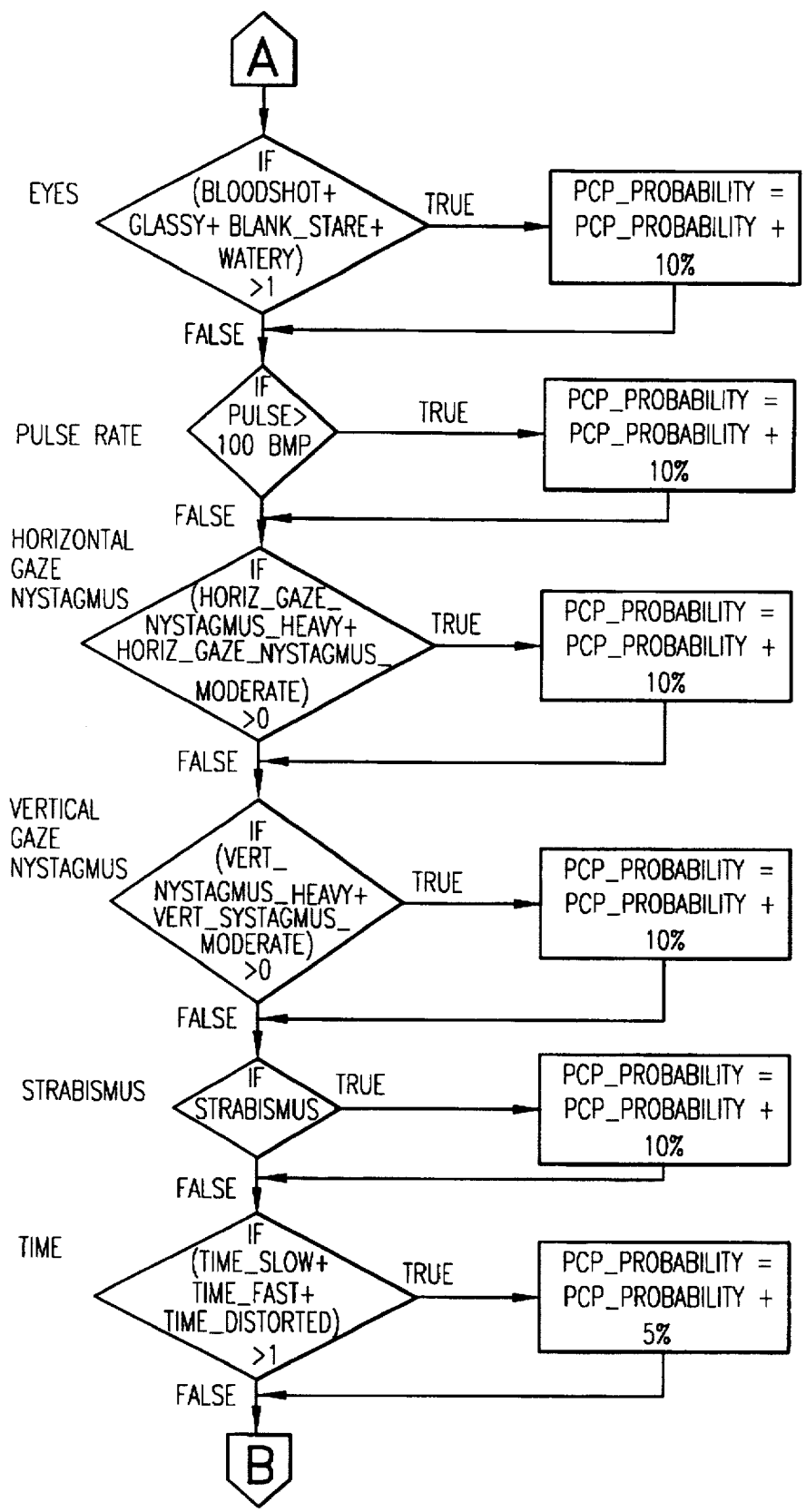
Figure 1P:
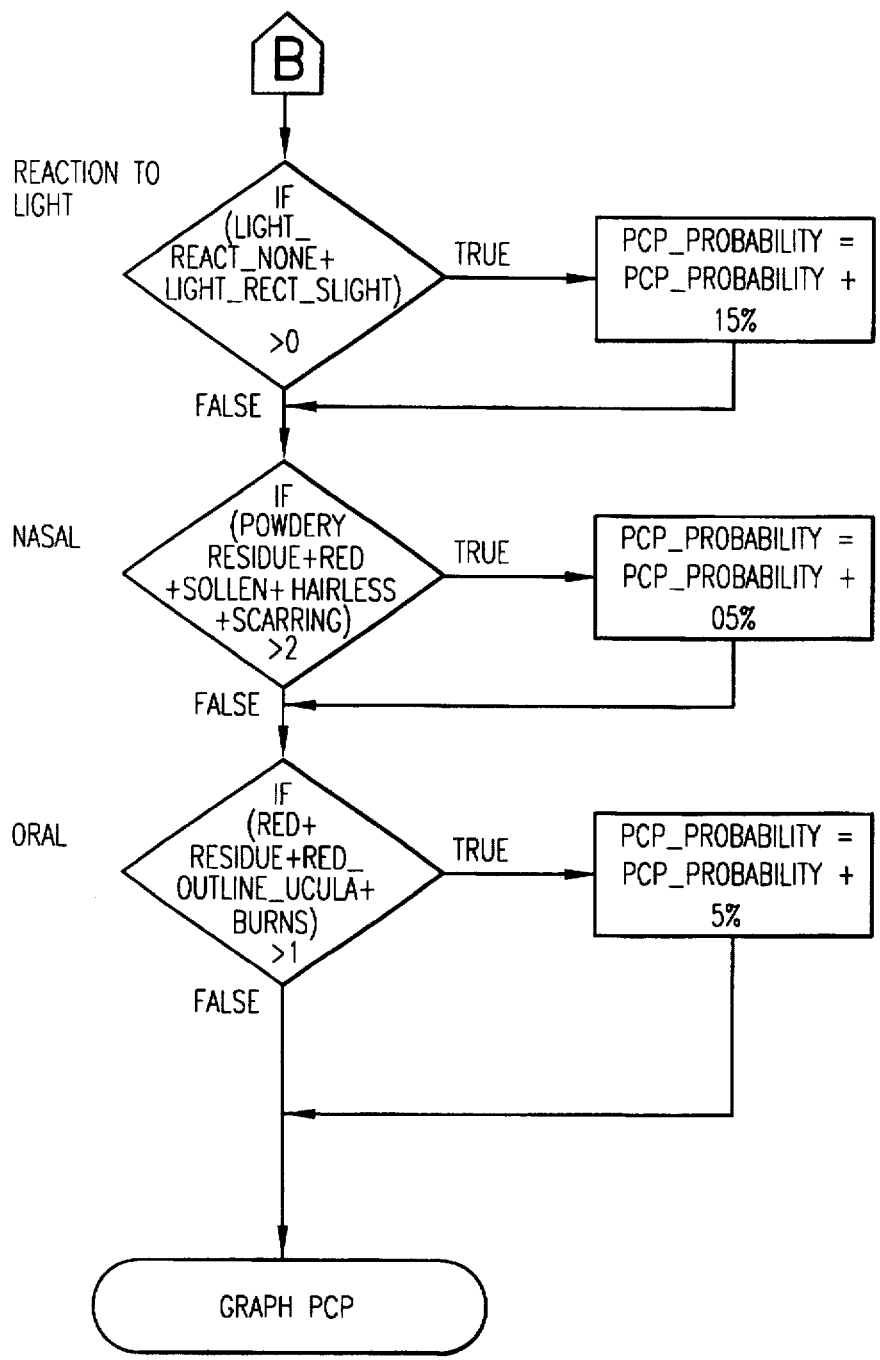
Figure 1Q:
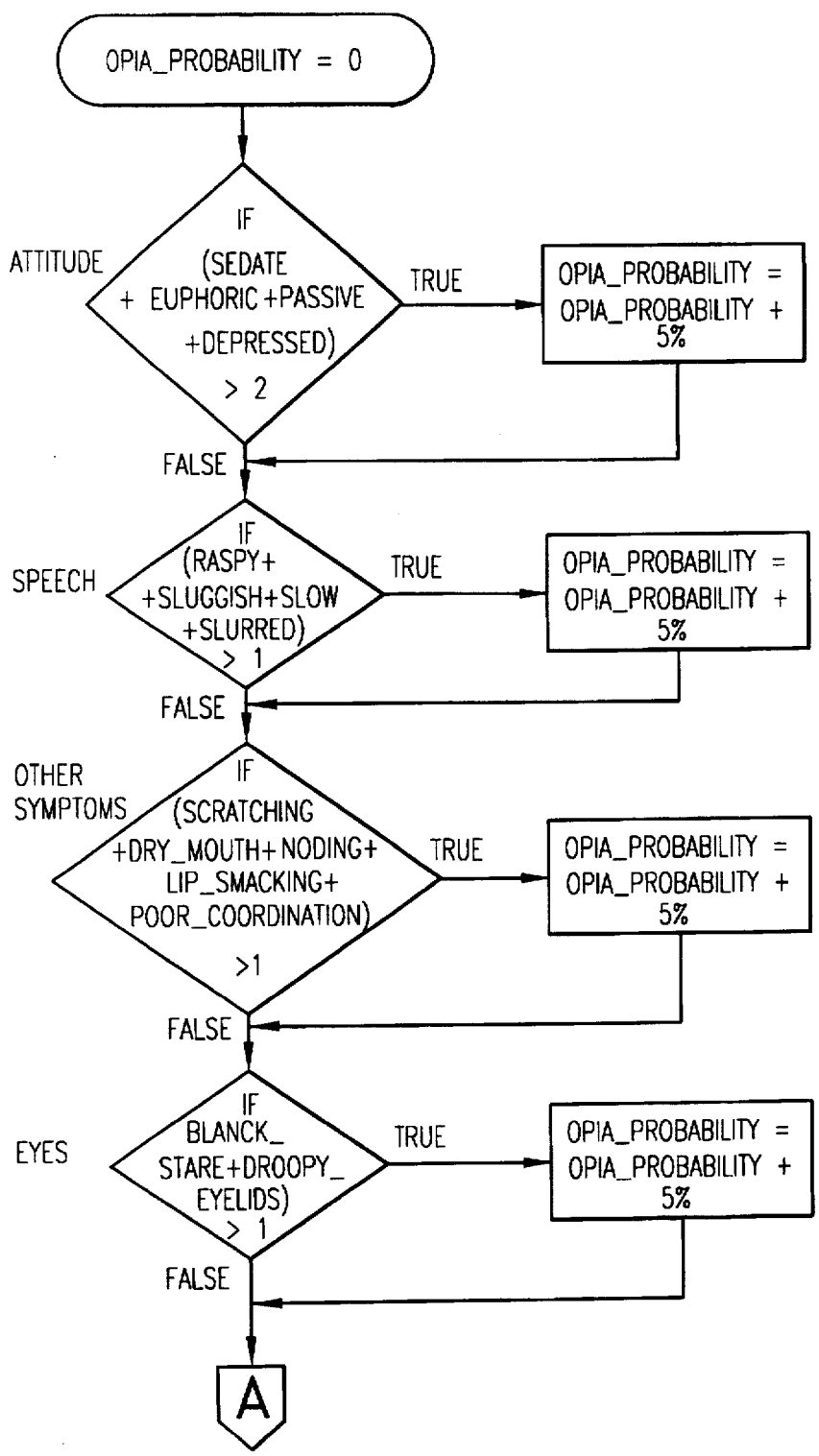
Figure 1R:
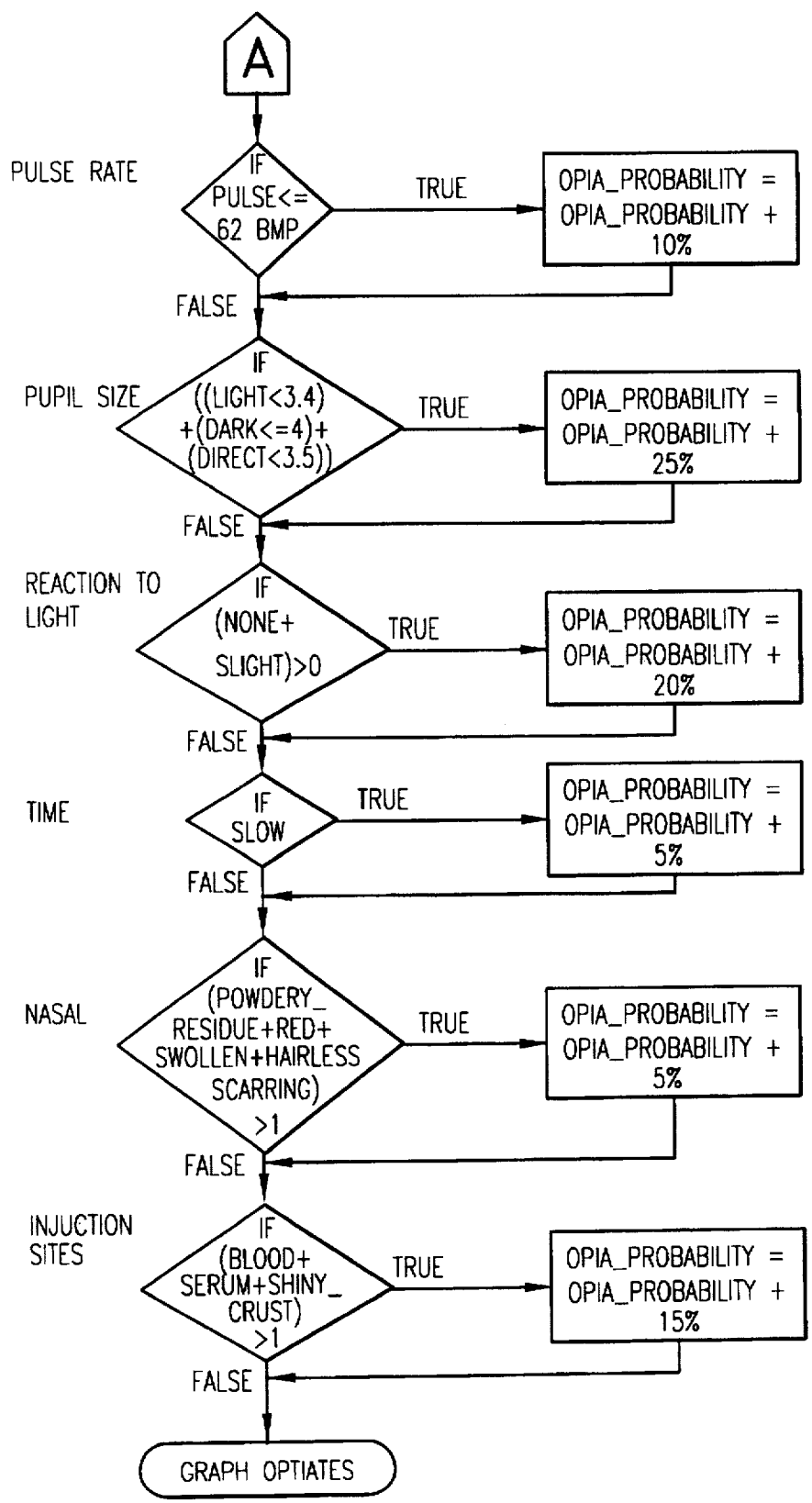
Figure 1S:
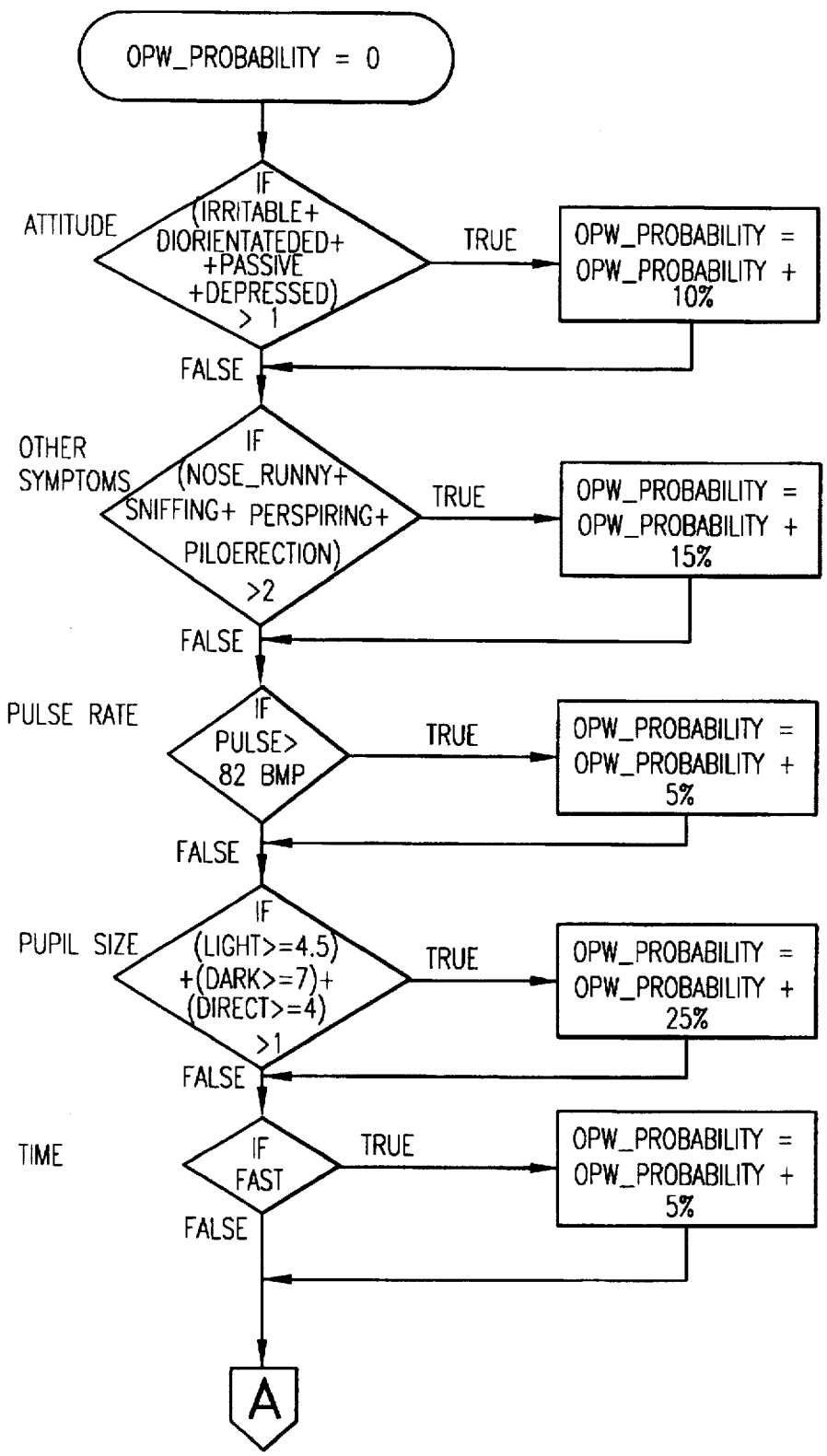
Figure 1T:
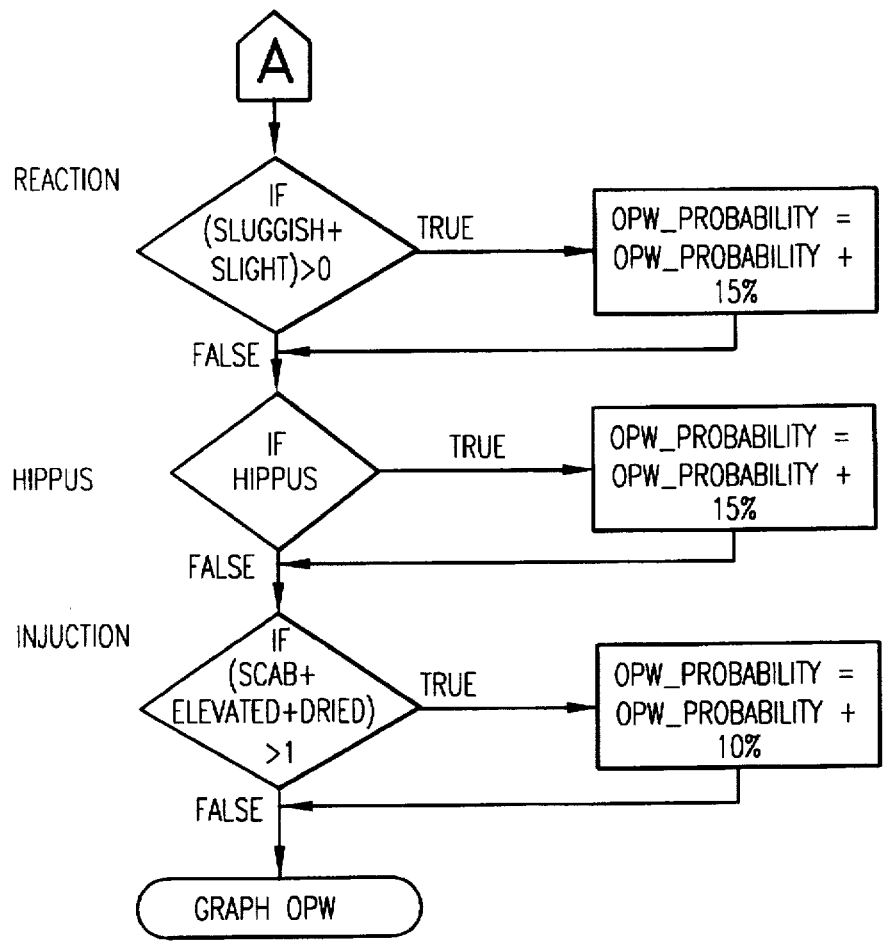
Figure 9:
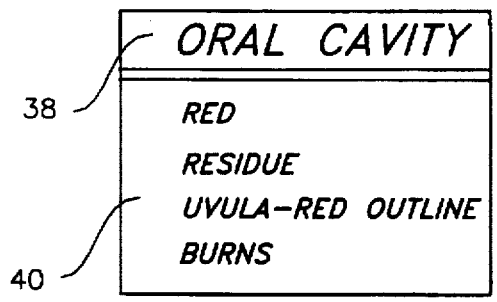
Figure 12:
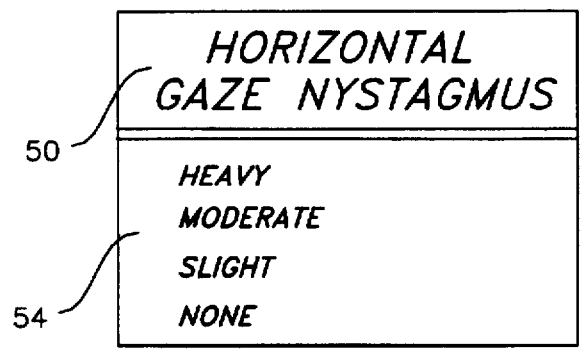
Figure 10:
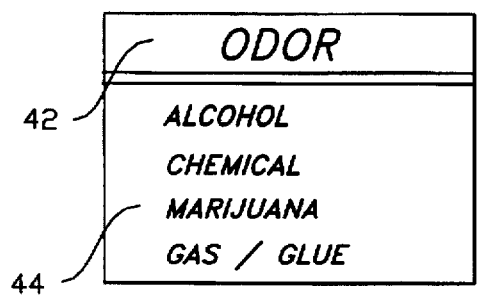
Figure 13:
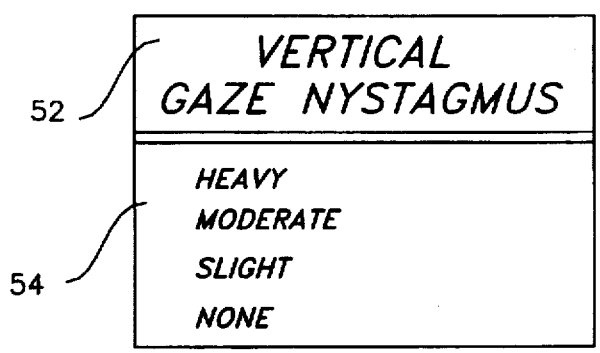
Figure 11:
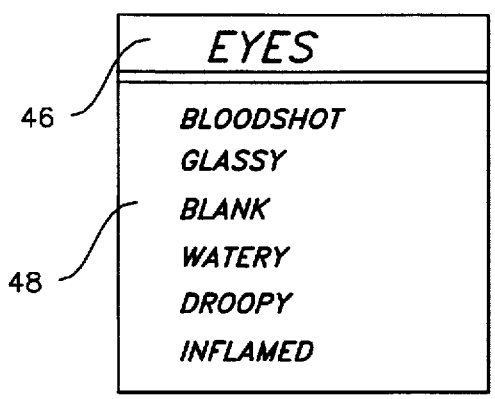
Figure 14:
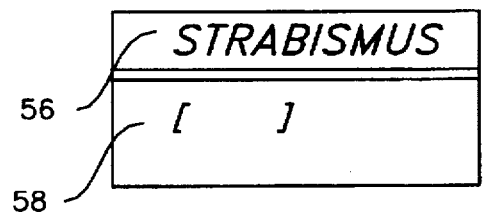

As the present system will be understood to be exercised with the use of a computer, it will be appreciated that any class of such apparatus may be employed, such as a PC, XT, AT or other type including a micro-processor, storage device and output device, the latter including at least a monitor (CRT) and preferably also a printer. These components are all well known in the art and need not be illustrated herein.

The present drug recognition screening evaluation is a systematic, standardized method of screening a suspect individual to determine whether the person is under the influence of drugs or has recently used drugs and may be employed to accurately detect drug use for a period of up to seventy-two hours after ingestion. During use of the system, should medical conditions become apparent that could interfere with the validity of the evaluation, these are indicated, with instructions being displayed as to the appropriate steps to be taken. A trained drug recognition expert operates the software program as outlined in the flow chart 10 in FIG. 1 to arrive at the conclusion shown in the graphical display 12 of FIG. 19.

Upon running the program, an initial screen is presented, calling for the operator to enter general data representing items applicable to the individual being screened, rather than physiological observations by the operator. Depending upon the client's responses to certain medical background queries such as prescription medications, methadone, glaucoma, diabetes, syphilis, epilepsy, head injuries and admission to use of any of listed classes of drugs, the screening program may terminate at this point with a recommendation that a urine test be conducted or medical evaluation be sought. On the other hand, specific responses as input by the operator will advance the program to succeeding screens, presenting menus depicting a plurality of categories of physiological observations to be made by the trained operator.

At this point, the skill of the trained operator comes into play as each of the categories of behavioral/physical symptoms are evaluated with a positive response entered by the operator for each symptom or element recognized. The sequence of proffered symptom categories shown in FIGS. 3-18 is representative of a typical flow of the presented queries sequentially displayed on the operator's monitor and the order thereof may be altered, although the flow as disclosed herein has been found to be a most logical presentation as it allows for the earliest culmination of the screening process should any cumulative responses lead to a determination that a urine test or medical evaluation is indicated at any point during execution of the program.

FIG. 2 of the drawings illustrates a typical screen presentation 14 that may appear before the operator during the execution of the program and which calls for the operator to consider the suspect individual with respect to each physical category as the cursor is cycled through each element under each category. As the operator observes the individual, any physical parameter believed to be positive is tagged in any well known manner, such as by hitting the ENTER key on the computer keyboard. An initial physical category 16 may be that of the client's SPEECH and as shown in FIG. 3, there are ten elements 18 presented comprising: deliberate, sluggish, clear/steady, slow, thick-slurred, repetitive, raspy, rapid, unresponsive and incoherent. As the operator carefully considers each of these 10 elements, any ones that are applicable to the case at hand are answered in the affirmative. This is accomplished as mentioned above, through any suitable keyboard input such as by scrolling a cursor through the choices of elements presented and hitting the ENTER key where applicable, thereby tagging each such element as positive, on the screen and within the program. It will be understood that according to the particular situation at hand, one or any number of the menu choices in any one category may be selected. Upon completing the choices in any one category and moving on to the next, the program has tagged those choices and summed the total number of elements so tagged. This feature forms the basis for the database of information contained in the software to enable the final determination resulting in the ultimate analysis, as will be seen hereinafter.

Following entry of applicable parameters relating to the individual's SPEECH, consideration is made of the category 20 concerning the subject's PULSE (FIG. 4) and following taking of the client's pulse, its rate in BPM is entered from the keyboard as element 22, where called for in the menu. Next, the operator notes the six elements 24 under the menu category 26 of INJECTIONS (FIG. 5), with positive inputs being made from the keyboard for any one(s) of the elements: blood, serum, shiny crust, scab, lift and dried. These elements 24 may be readily confirmed upon a careful examination of the client's arms and backs of each hand.

In a succeeding menu, the category 26, PUPIL SIZE (FIG. 6) appears and this category is the only remaining one wherein a measuring device is called for in order to determine the proper input. The operator conducts a measurement of the size of both pupils and inputs the results in mm. to complete each of the three elements for each eye in this category, namely a measurement conducted under: room light, darkness and direct light, for each eye. Next, the menu category 30 directed to REACTION TO LIGHT (FIG. 7) is responded to by observing which of the four elements none, slight, sluggish or normally reactive is appropriate.

There are six elements 34 to be considered under the category 36 relating to NASAL CAVITY (FIG. 8) and these are responded to as appropriate. One or more of the elements powdery residue, red, swollen, hairless, scarring or not unusual may be recorded as positive by the operator. Under the category 38 concerning ORAL CAVITY (FIG. 9), appropriate input is made for a positive observation of the four elements 40 comprising red, residue, red outline around uvula and burns. Upon reaching category 42 concerning ODOR (FIG. 10), the operator replies affirmatively for any of the four elements 44 comprising alcohol, chemical, marijuana and gasoline/glue.

Upon reaching the EYES category 46 (FIG. 11) which concerns general observations pertinent to the client's eyes, input is made for any applicable ones of the six elements 48 identified as bloodshot, glassy, blank stare, watery, droopy eyelids and inflamed.

The subject's eyes are observed for nystagmus and this is conducted under both the category 50 of HORIZONTAL GAZE NYSTAGMUS (FIG. 12) and the category 52 of VERTICAL GAZE NYSTAGMUS (FIG. 13) with each category containing the four element choices 54 of heavy, moderate, slight and none. A succeeding category 56 directed to STRABISMUS (FIG. 14) contains a single element representing a positive observation and if this condition is observed, the entry 58 is tagged before moving on the next menu category 60 relating to ATTITUDE (FIG. 15), containing the fifteen elements 62 including not unusual, sedated, agitated, hallucinating, euphoric, combative, irritable, argumentative, stuporous, erratic, disoriented, bizarre, passive, depressed and excited.

A next category of physical observations comprises the OTHER SYMPTOMS (FIG. 16) category 64 and includes the ten elements 66 comprising scratching, dry mouth, nose runny, sniffing, on the nod, perspiring, lip smacking, coordination poor, slow responses and piloerection. As before, input is made to identify as positive any of these elements 66 which apply. A following category 68 identified as HIPPUS (FIG. 17) includes two element choice 70 and 72 with either element being tagged when observed positive.

A remaining menu category 74 having a plurality of elements assigned variable values during execution of the software scoring scheme comprises the THIRTY SECOND TIMING COUNT (FIG. 18) and includes the four (4) elements 76 comprising normal, distorted, fast and slow.

Although not replicated in a drawing figure, another menu item of CLIENT ADMITS USING may be included to present a menu identifying each of the seven classes of drugs being screened and whereupon the subject is queried as to each of the seven elements, with a positive response being so input where applicable and accordingly influencing the resultant evaluation should any of the scoring schemes utilized by the software border on a marginal decision.

As mentioned before, if any single entry indicates that a valid identification of drug use can not be determined from the input response, a recommendation will be presented that either a urine test be secured or medical evaluation be sought. This same recommendation may also appear at any time a cumulative number of input responses results in the same conclusion.

Figure 19:
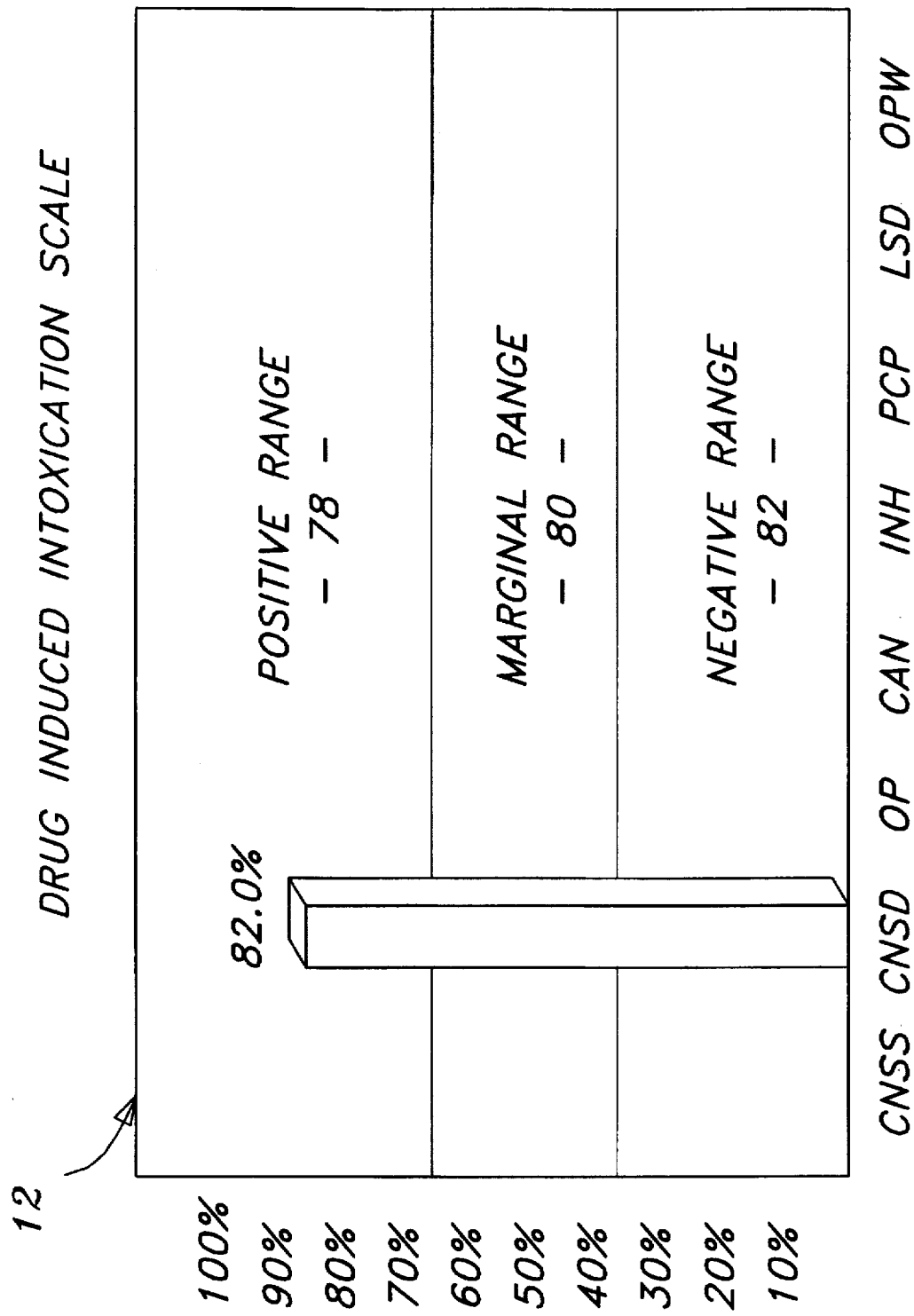
FIG. 19 is a chart illustrating an example of the graphical display yielded following operation of the system's software.

With all of the foregoing input having been accomplished and no recommendation as above appears, a succeeding screen appears with a graphical representation 12 such as shown in FIG. 19. This graph contains an X-axis listing the seven drug classes CNSS, CNSD OP, CAN, INH, PCP AND LSD together with an additional class OPW (opiate withdrawal) and illustrates a drug induced intoxication scale as calculated by the program for the listed classes. The Y-axis will be seen to comprise a percentage range divided into three sub-ranges, negative, marginal and positive. The software has determined that the subject being screened has been analyzed positive for any Y-axis entry extending greater than 70%, or into the positive sub-range 78, while any drug entry falling between the 30% and 70% range of the marginal sub-range 80 may be considered of marginal value in accessing the evaluation system. Those drug classes depicted below the 30% range or in the negative sub-range 82, may be ruled out in this screening process. It will be understood that multiple drug classes may be recorded within the positive range and this will indicate either multiple drug use or drug use that can cause similar physiological symptoms. The highest rated percentage will be the dominant drug and a subsequent urine test is likely to test positive for that dominant drug class and may also test positive for any other drug classes appearing in the positive range.

The weighting and rationale as applied by the software in determining the analysis as reflected in the graph of FIG. 19 will now be described. As previously mentioned, the determination of the likelihood of any one of the drug classes being involved when executing the present system is calculated in consideration of the specific elements which have been selected, or the values as have been entered, while addressing each of the menus and categories of the program. Additionally, the total number of elements in each category will have an effect upon the ultimate analysis appearing in the graph of FIG. 19. Each category is in turn allocated a percentage value in arriving at the final screening results. These percentages reflect a frequency of each element to a particular drug, deviation from the norm and relevancy of the element to a specific drug class while a minimum number of positive or tagged inputs among the plurality of elements of each category have been assigned to represent the number and identity of individual symptoms that would indicate significance to an element as calculated to correlate to a specific drug class.

First, the weighting schedule as applied to the drug class of central nervous system depressants (CNSD) will be reviewed. These drugs, which slow down the operation of the brain, comprise alcohol, barbiturates, non-barbiturates, anti-anxiety tranquilizers, anti-depressants, anti-psychotic tranquilizers and combinations of the above. The first table below identifies the percentage applied to each category and the minimum number of particular ones of the elements in that category which must be recorded in the menu input in order for a CNSD drug to appear in the positive range of the graph of FIG. 18.

Upon examination of the Tables relating to the various drug classes, it will become apparent that different rating schemes are followed as the program analyzes the probability of an individual's drug use. That is, the weight in percentile will be seen to vary for the same categories appearing in the rating of different drug classes and additionally, the minimum number of 'hits' or positive responses among different ones of the elements for certain categories will vary between the scoring or evaluation associated with each drug class.

To appreciate the referenced scoring scheme as applicable to any one of the drug classes, if an operator were to input at least the minimum number of elements shown for each and every listed category and no other elements not listed for each category were tagged as positive then, the resultant graphical display of FIG. 18 would show that drug class in the positive range, at or near 100%.

TABLE I

| (CNSD) | | |
|---|---|---|
| Category | % | Min. Nr. Of Specified Elements |
| Attitude | 10 | 3 - sedated, euphoric, stuporous, passive, disoriented, depressed |
| Speech | 10 | 3 - deliberate, sluggish, slow, incoherent, thick/slurred, unresponsive |
| Other symptoms | 10 | 2 - dry mouth, coordination poor, nodding, slow responses |
| Odor | 10 | 1 - alcohol |
| Eyes | 10 | 2 - blank stares, droopy eyelids, glossy |
| Pulse rate | 30 | >25 BPM & less than or = 62 BPM |
| Nystagmus (horiz) | 30 | 1 - heavy, moderate |
| Nystagmus (vert.) | 20 | 1 - heavy, moderate |
| Strabismus | 10 | 1 - (Yes) |
| Time | 10 | 1 - distorted, slow |
| React. to light | 50 | 1 - sluggish |

Table II below depicts the above mentioned scoring values and minimum number of specific ones of the elements for those categories applicable during the evaluation by the program for probable use of central nervous system stimulants (CNSS). These drugs serve to speed up the operation of the brain and spinal cord and comprise cocaine, methamphetamine (ICE), amphetamine sulfate and amphetamines including dexedrine, benzadrine, biphetamine and desoxyn.

TABLE II

| (CNSS) | | |
|---|---|---|
| Category | % | Min. Nr. of Specified Elements |
| Attitude | 10 | 2 - euphoric, erratic, excited Disoriented |
| Speech | 10 | 1 - rapid |
| Other symptoms | 10 | 2 - dry mouth, nose runny, sniffing, Perspiring, scratching |
| Pupil size | 60 | 2   Room light >4.4 mm Dark >6.9 mm |

TABLE II-continued

(CNSS)

| Category | % | Min. Nr. of Specified Elements |  |
|---|---|---|---|
|  |  |  | Direct >3.9 mm) |
| Pulse rate | 20 |  | >100 BPM |
| Nystagmus (horiz) | 10 | 1 | moderate, slight |
| Time | 10 | 1 | fast |
| React. to light | 20 | 1 | slight, sluggish |
| Hippus | 10 | 1 | (Yes) |
| Nasal cavity | 30 | 2 | powdery residue, red, swollen, hairless, scarring |
| Oral cavity | 5 | 1 | red, red outline, burns |
| Injection | 5 | 2 | blood, serum, shiny crust |

Follows is Table III, directed to the scoring scheme as applicable to phencyclidine (PCP). This drug is assigned its own class due to the fact that in some individuals it acts as an hallucinogen while in others it may act as a stimulant or a depressant.

TABLE III

(PCP)

| Category | % | Min. Nr. of Specified Elements |  |
|---|---|---|---|
| Attitude | 10 | 5 - | sedated, agitated, hallucinating, euphoric, combative, argumentative, irritable, erratic, disoriented, bizarre, passive |
| Speech | 10 | 3 - | repetitive, unresponsive, slow, Incoherent, thick/slurred |
| Odor | 20 | 1 - | chemical |
| Other symptoms | 10 | 1 - | perspiring, poor coordination |
| Eyes | 10 | 2 - | bloodshot, glassy, blank stare, watery |
| Pulse rate | 20 |  | >100 BPM |
| Nystagmus (horiz) | 20 | 1 - | heavy, moderate |
| Nystagmus (vert.) | 20 | 1 - | heavy, moderate |
| Strabismus | 20 | 1 - | (Yes) |
| Time | 10 | 1 - | slow, fast, distorted |
| React. to light | 30 | 1 - | none, slight |
| Nasal | 10 | 1 - | powdery residue, red, swollen, Hairless, scarring |
| Oral | 10 | 1 - | red, residue, burns, red outline around uvula |

The next class of drugs, inhalants, comprises breathable chemicals that produce a mind altering result and include: volatile solvents such as glue, gasoline and petroleum products; aerosols which include chemicals discharged from pressurized containers; and anesthetics which involve chemicals used during surgery that produce semi-consciousness. Table IV below depicts the scoring scheme applicable to this class of drugs.

TABLE IV

(Inhalants)

| Category | % | Min. Nr. of Specified Elements |  |
|---|---|---|---|
| Attitude | 10 | 4 - | agitated, hallucinations, erratic, euphoric, stuporous, disorientated, bizarre |
| Speech | 10 | 2 - | thick/slurred, incoherent, unresponsive |
| Odor | 70 | 1 - | gas, glue |
| Other symptoms | 10 | 1 - | nose runny, coordination poor |
| Eyes | 20 | 2 - | bloodshot, watery, inflamed |
| Pulse rate | 10 |  | >90 BPM |
| Nystagmus (horiz) | 20 | 1 - | heavy, moderate |

TABLE IV-continued

(Inhalants)

| Category | % | Min. Nr. of Specified Elements |  |
|---|---|---|---|
| Nystagmus (vert.) | 20 | 1 - | heavy, moderate |
| Strabismus | 20 | 1 - | (Yes) |
| Time | 10 | 1 - | distorted |

To grasp the scoring scheme applicable to the class of drugs known as hallucinogens, reference is made to Table V below. These drugs are known to produce hallucinations and include the synthetic versions lysergic acid diethylamide (LSD), methylenedioxyamphetamine (MDA), methoxy-MDA (MMDA), trimethoxyamphetamine (TMA), serenity-tranquility-peace (STP), diethyltryptamine (DET) and dimethyltryptamine (DMT) while natural versions include peyote and psilocybin.

TABLE V

(Hallucinogens)

| Category | % | Min. Nr. of Specified Elements |  |
|---|---|---|---|
| Attitude | 30 | 3 - | agitated, hallucinating, euphoric, argumentative, erratic, bizarre, disoriented |
| Speech | 20 | 2 - | unresponsive, incoherent, rapid |
| Other symptoms | 40 | 2 - | perspiring, poor coordination, piloerection |
| Eyes | 20 | 1 - | watery |
| Pulse rate | 20 |  | >90 BPM |
| Pupil size | 60 | 2 - | room light, >4.0 mm dark, >6.9 mm direct, >3.9 mm |
| Time | 10 | 1 - | distorted fast |

The scoring scheme applied in evaluating for cannabinoids appears in the following Table VI. This class of drugs which is derived from the cannabis sativa plant comprises the active ingredient delta-9 tetrahydrocannabinol (THC) and appears in the form of marijuana, hashish or hashish oil.

TABLE VI

(Cannabinoids)

| Category | % | Min. Nr. of Specified Elements |  |
|---|---|---|---|
| Attitude | 10 | 3 - | sedated, hallucinating, irritable, euphoric, disoriented, bizarre, passive, depressed |
| Speech | 10 | 2 - | sluggish, slow, repetitive, raspy unresponsive |
| Odor | 20 | 1 - | marijuana |
| Other symptoms | 10 | 2 - | dry mouth, poor coordination, slow responses |
| Eyes | 20 | 2 - | bloodshot, glassy, blank stare, watery droopy eyelids |
| Pulse rate | 10 |  | >85 BPM |
| Strabismus | 20 | 1 - | (Yes) |
| Pupil size | 30 | 2 - | room light, >3.9 mm & <6.1 mm dark, >6.5 mm & <7.6 mm direct, >3.5 mm & <4.6 mm |
| Time | 10 | 1 - | fast, distorted |
| Reaction | 10 | 1 - | sluggish |
| Rebound hippus | 20 | 1 - | (Yes) |
| Oral cavity | 30 | 1 - | residue, red outline, burns |

Table VII below relates the scoring scheme for the opiates class of drugs and which comprise natural derivatives of opium as well as synthetic opiates as chemically produced from a variety of substances but which exhibit effects virtually identical to the effects of natural opiates. The natural opiates include powdered opium, morphine, codeine, heroin (diacetyl morphine), dilaudid, hycodan and percodan while synthetic opiates include demerol, methadone, numorphan and fentanyls.

TABLE VII (Opiates)

| Category | % | Min. Nr. of Specified Elements |
|---|---|---|
| Attitude | 10 | 2 - sedated, euphoric, passive, depressed |
| Speech | 10 | 2 - raspy, sluggish, slow, thick/slurred |
| Other symptoms | 10 | 3 - scratching, dry mouth, modding, lip smacking, poor coordination |
| Eyes | 10 | 1 - blank stare, droopy eyelids |
| Pulse rate | 20 | <63 BPM |
| Pupil size | 50 | 2 - room light, <3.5 mm<br>dark, <4.1 mm<br>direct, <3.5 mm |
| React. to light | 40 | 1 - none, slight |
| Time | 10 | 1 - slow (over 30) |
| Nasal | 10 | 2 - powdery residue, red, swollen, hairless, scarring |
| Injections | 30 | 2 - blood, serum, shiny crust |

The remaining drug class being screened involves an individual who is on opiate withdrawal and the Table VIII below sets forth the scoring scheme applicable in those instances wherein an insufficient level of the drug is in the blood to cause specific symptoms when the individual has reached the dependence stage.

TABLE VIII (Opiate withdrawal)

| Category | % | Min. Nr. of Specific Elements |
|---|---|---|
| Attitude | 20 | 2 - irritable, disoriented, passive, depressed |
| Other symptoms | 30 | 3 - nose runny, sniffing, perspiring, piloerection |
| Pulse rate | 10 | >82 BPM |
| Pupil size | 50 | 2 - room light, >4.4 mm<br>dark, >6.9 mm<br>direct, >3.9 mm |
| Time | 10 | 1 - fast (under 30) |
| Reaction | 30 | 1 - sluggish, slight |
| Hippus | 30 | 1 - (Yes) |
| Injection | 20 | 2 - scab, elevated, dried |

Following presentation of the graph as in FIG. 19, a monitor display will appear and which presents a narrative explanation of the screening results appearing in the graph. For example, if the subject client's screening should show a definite positive use of a CNSS, a narrative explanation along the lines of the following will appear:

POSITIVE FOR CENTRAL NERVOUS SYSTEM STIMULANTS

The subject's test interpretation indicates that they are currently under the influence of a Central Nervous System Stimulant. Current use indicates that the person Has introduced a Central Nervous System Stimulant into their body within the previous seventy-two hour period prior to the administration of this test. Please explore for substances that are classified as CNS Stimulants by this screening system. A list of CNSS are below:

Cocaine
Amphetamines
Methamphetamine (ICE)
Amphetamine Sulfate

It is recommended that the individual be referred for a urine screen for the above substances. The average urine detection period for Cocaine is from twelve (12) hours to three (3) days. The average urine detection period for Amphetamines, Methamphetamines and Amphetamine Sulfate is from one (1) hour to two (2) days. It is important to note that another popular Amphetamine analogue, Methylenedioxymethamphetamine, sometimes called XTC will not be detected in the urine screen as an amphetamine. A special urine screen for this amphetamine analogue must be requested. Please note that average detection periods in EMIT and/or TLC testing vary and detection periods should be viewed as estimates.

From the foregoing it will be appreciated that an improved drug screening evaluation system has been developed and wherein, by passive observations, a trained operator is able to observe and tag those physical parameters in each of a plurality of categories that a suspect individual exhibits, with associated software applying various weights or values to each parameter so tagged. These values are assigned in accordance with the total number and particular identification of those parameters as tagged in each category to arrive at a graphical display identifying those class(es) of drugs suspected of having been ingested by the subject.

It will be understood that the present invention is not limited to the sole embodiment described hereinabove, but encompasses any and all embodiments within the scope of the appended claims.

I claim:

1. A method of conducting a drug screening of an individual through use of a computer having an output device and an input device and loaded with software, the method comprising the steps of:

presenting to an operator a series of menus on the output device, wherein the menus comprise a plurality of categories containing a plurality of physical elements;

observing, by the operator, physical parameters exhibited by the individual;

selecting through the input device in response to the menus presented on the output device those physical elements that correspond to said observed physical parameters exhibited by the individual;

assigning with the software various values to said selected physical elements;

calculating with the computer a probability of recent drug use of at least one class of drugs using the assigned values; and, presenting on said output device the probability, of recent drug use by the individual of at least one class of drugs.

2. The method according to claim 1 wherein, said plurality of categories include the categories of attitude, speech, odor, other symptoms, eyes, nasal cavity, oral cavity and injections.

3. The method according to claim 1 further comprising recognizing with the software any combination of selected physical elements indicative of an inaccurate determination.

4. The method according to claim 1 including, receiving on said output device following receipt of said probability of recent drug use, a narrative explaining the extent and value of said probability of recent drug use, what drug(s) could have contributed to said probability of recent drug use and whether further action is recommended.

5. The method according to claim 1 wherein, said presenting step includes a graphical display presenting three sub-ranges respectively indicating negative, marginal and positive ratings for probable drug use by the individual.

6. A non-invasive system enabling an operator to screen an individual for the ingestion of drugs comprising;

a computer having input and output devices and loaded with software, said input device including a keyboard and said output device including a monitor, said software presenting on said monitor a screen exhibiting a plurality of categories listing observable physical elements which the operator selects from and tags when a positive condition is observed in the individual, said software identifying which of said physical elements in each said category are pertinent in the determination of probable drug use in each of a plurality of drug classes, said software applying varying weights to each said physical element as it applies in the determination of any one drug class and noting the sum of said tagged physical elements to arrive at a conclusion as to probable drug use by the individual, and said monitor presenting a display of a probability of use by the individual of drugs in each of said plurality of drug classes.

7. The non-invasive system according to claim 6 wherein, said display on said monitor comprises a graph listing said plurality of drug classes along an X-axis and said probability of drug use along a Y-axis.

8. The non-invasive system according to claim 7 including, a plurality of sub-ranges on said graph respectively representing negative, marginal and positive ranges of probability of drug use along said Y-axis.

* * * * *